(12) United States Patent
Krantz

(10) Patent No.: US 7,927,579 B2
(45) Date of Patent: Apr. 19, 2011

(54) TANDEM ANALYSES OF NONCOVALENTLY DRIVEN EFFECTORS FOR MODULATORY MAPPING OF ACTIVITIES OF PROTEIN SITES

(75) Inventor: Alexander Krantz, San Francisco, CA (US)

(73) Assignee: Advanced Proteome Therapeutics, Inc, San Francisco, CA (US)

( * ) Notice: Subject to any disclaimer, the term of this patent is extended or adjusted under 35 U.S.C. 154(b) by 1515 days.

(21) Appl. No.: 10/759,513

(22) Filed: Jan. 16, 2004

(65) Prior Publication Data

US 2004/0176575 A1 Sep. 9, 2004

Related U.S. Application Data

(60) Provisional application No. 60/440,632, filed on Jan. 17, 2003.

(51) Int. Cl.
*A61K 51/00* (2006.01)

(52) U.S. Cl. .................... 424/1.69; 424/9.322; 424/9.34; 435/4; 435/7.1

(58) Field of Classification Search .................. 435/174, 435/177, 178, 180, 181, 183, 184, 188, 964; 436/518, 528, 529, 531, 532, 174; 530/345, 530/402–411; 544/224, 232, 239
See application file for complete search history.

(56) References Cited

U.S. PATENT DOCUMENTS

| | | | |
|---|---|---|---|
| 5,840,733 A | 11/1998 | Krantz et al. | |
| 5,942,620 A | 8/1999 | Krantz et al. | |
| 6,013,792 A | 1/2000 | Castelhano et al. | |
| 6,107,489 A | 8/2000 | Krantz et al. | |
| 6,277,583 B1 | 8/2001 | Krantz et al. | |
| 6,277,863 B1 | 8/2001 | Krantz et al. | |
| 6,303,569 B1 * | 10/2001 | Greenwald et al. | 514/2 |
| 6,335,155 B1 * | 1/2002 | Wells et al. | 435/4 |
| 6,403,324 B1 | 6/2002 | Krantz et al. | |
| 6,936,597 B2 * | 8/2005 | Greenwald et al. | 514/49 |
| 2002/0064799 A1 | 5/2002 | Cravatt et al. | |
| 2005/0037974 A1 | 2/2005 | Krantz et al. | |

FOREIGN PATENT DOCUMENTS

| | | |
|---|---|---|
| EP | 1056474 B1 | 6/2002 |
| EP | 0956049 B1 | 10/2002 |
| WO | WO-97/25074 A2 | 7/1997 |
| WO | WO-97/29372 A1 | 8/1997 |
| WO | WO-98/00171 A2 | 1/1998 |
| WO | WO-99/24075 A2 | 5/1999 |

(Continued)

OTHER PUBLICATIONS

Birkenmeier, G. & Kopperschlager, G. Detection of conformational changes in proteins by probing with poly(ethylene glycol)-bound ligands. Methods Enzymol. 1994;228:264-275.*

(Continued)

*Primary Examiner* — N. C. Yang
(74) *Attorney, Agent, or Firm* — Nelson Mullins Riley & Scarborough LLP; Brian C. Trinque

(57) ABSTRACT

The present invention provides methods of discovering and mapping secondary binding sites on biological molecules (e.g., proteins), the effects, if any, of site occupancy on the primary function of the molecule, and the screening of small molecules against the secondary binding sites. The invention further provides novel complexes for modification of secondary binding sites and the resulting modified biological molecules.

13 Claims, 9 Drawing Sheets

FOREIGN PATENT DOCUMENTS

| WO | WO-99/24076 A2 | 5/1999 |
|---|---|---|
| WO | WO-99/24462 A2 | 5/1999 |
| WO | WO-02/063271 A2 | 8/2002 |

OTHER PUBLICATIONS

Ingham, K.C. Protein precipitation with polyethylene glycol. Methods Enzymol. 1984;104:351-356.*

Johansson, G. Affinity partitioning. Methods Enzymol. 1984;104:356-364.*

International Search Report and Written Opinion from WO 04/066917.

Database Biosis Accession No. PREV198018031914, (1979).

Evans, Bettie et al., "Inactivation of Cathepsin B by Active Site-directed Disulfide Exchange, Application in Covalent Affinity Chromatography," *The Journal of Biological Chemistry*, vol. 258(17):10227-10232 (1983).

Leelasvatanakij, L. et al., "A solid-phase synthetic strategy for the preparation of peptide-based affinity labels: synthesis of dynorphin A analogs," *J. Peptide Res.*, vol. 56:80-87 (2000).

Powers, Stephen P. et al., "Use of Photoaffinity Probes Containing Poly(ethylene glycol) Spacers for Topographical Mapping of the Cholecystokinin Receptor Complex," *Biochemistry*, vol. 30:676-682 (1991).

Ruppert, Jim et al., "Automatic identification and representation of protein binding sites for molecular docking," *Protein Science*, vol. 6:524-533 (1997).

Smith, Geoffrey B. et al., "Functional domains of $GABA_A$ receptors," *Trends in Pharmacological Sciences*, vol. 16(5):162-168 (1995).

European Office Action for Application No. 04702918.6, dated Apr. 1, 2008.

* cited by examiner

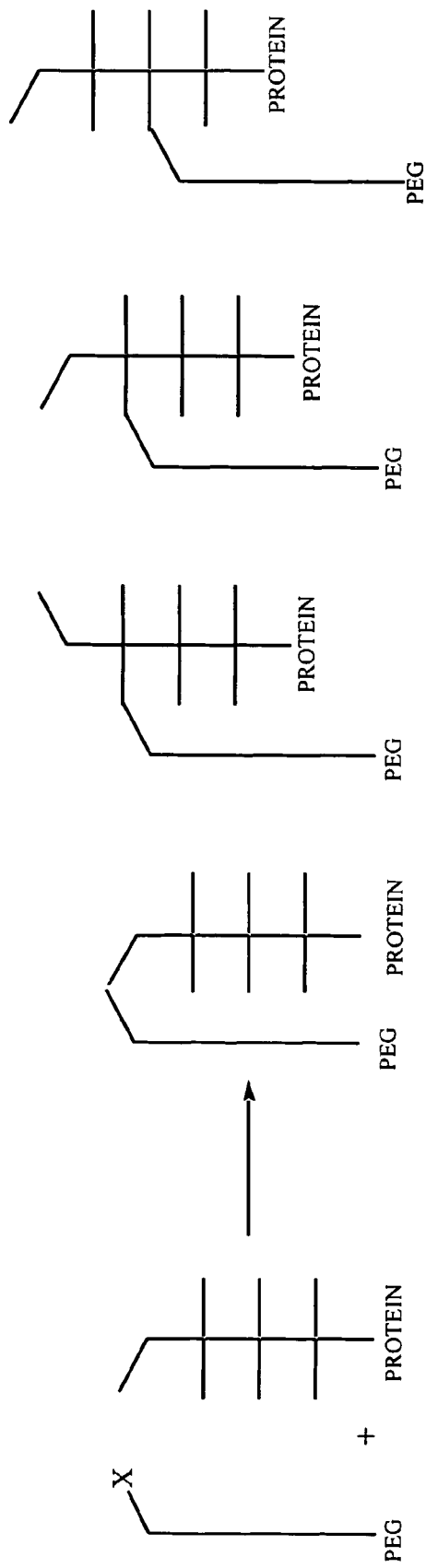

SEQUENCE LISTING

<160> NUMBER OF SEQ ID NOS: 3

<210> SEQ ID NO 1
<211> LENGTH: 4
<212> TYPE: PRT

-continued

<213> ORGANISM: Artificial Sequence
<220> FEATURE:
<223> OTHER INFORMATION: Description of Artificial Sequence: Synthetic
peptide

<400> SEQUENCE: 1

Ser Phe Asn Leu
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2

Thr Leu Asn Leu
1

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 3

Leu Gly Gln Gly Val Ser Ile Glu
1 5

TANDEM ANALYSES OF NONCOVALENTLY DRIVEN EFFECTORS FOR MODULATORY MAPPING OF ACTIVITIES OF PROTEIN SITES

RELATED APPLICATIONS

This application claims the benefit of U.S. Provisional Application No. 60/440,632, filed Jan. 17, 2003, which application is incorporated herein by this reference.

SEQUENCE LISTING

The instant application contains a Sequence Listing which has been submitted in ASCII format via EFS-Web and is hereby incorporated by reference in its entirety. Said ASCII copy, created on Feb. 24, 2011, is named 513485.txt and is 1,101 bytes in size.

FIELD OF THE INVENTION

The present invention relates generally to a systematic method of discovering secondary binding sites on a biological molecule (e.g., a protein), and compositions exploiting the secondary sites, such as the identification and use of complexes that bind to the secondary sites for the purpose of modulating the primary activity of the biological molecule and/or to attach a polymer in order improve the safety or efficacy of the biological molecule.

BACKGROUND

Conventional drug discovery is a complex iterative process in which "bets" are placed on drug leads which are then structurally modified and tested to provide clinical candidates meeting regulatory requirements. Successful drug development depends critically on proper choice of targets. Because of early decisions in the overall strategy for drug lead development, conventional programs are committed to a limited series of molecules from which only structurally related final candidates are selected. Conventional drug activity screens, however, are unable to produce a sufficiently diverse set of small molecule options as potential targets to expand opportunities for success. Developing the full potential for intervention strategies, therefore, depends not only on screening vast numbers of compounds against validated targets, but also on exploiting the full panoply of mechanisms and loci available for attack on any specific target, in a focused way. Despite this, drug development strategies, e.g., those that employ affinity labeling, continue to center on endogenous ligand binding sites. Strategies for systematically capitalizing on possible intervention sites along the entire surface of a biological molecule, e.g., a protein, have not yet evolved.

SUMMARY OF THE INVENTION

The present invention concerns methods and compositions for: (1) site-specific modification of a reactive group in or near a ligand binding site on a macromolecular biological target, particularly stable covalent bonding of such a reactive target group with a functional group linked to a ligand moiety and a polyalkylene oxide polymer; (2) discovery of novel binding sites, particularly sites other than sites for known endogenous ligands, on a biological target or region thereof with no explored secondary ligand binding site; and (3) discovery of ligands, typically in libraries, that bind such novel binding sites. In particular, the invention concerns ligands that are effector molecules and sites where binding of such effectors modulates (enhances or diminishes) activity of the target that comprises at least stable covalent bonding of a reactive target group. More precisely, the invention provides tandem analyses of covalent bonding of reactive groups and noncovalent binding of potential ligands which, combined, identify and map binding sites that are either nonmodulatory, where occupancy has no effect, or modulatory, where noncovalently driven effector binding modulates stable covalent bonding of a specific reactive target group and, preferably, correlated enzymatic or binding target activity. In short, the invention provides Tandem Analyses of Noncovalently Driven Effectors for Modulatory Mapping of Activities of Protein Sites, that is, "TandemMaps™".

It is an object of the present invention to provide a method for specifically or selectively modifying a particular target group on a biological target molecule, such as by covalent addition of an adduct such as a small drug molecule, a polymer (for instance, a polyalkylene oxide polymer such as polyethylene glycol) or another macromolecule (for instance, a targeting antibody), using a site-specific activated complex comprising a functional group linked to the adduct and a ligand moiety that binds to a ligand binding target site in or near the desired target reactive group.

Another major object of the invention is to provide a simple and rapid method for identifying and mapping, on a biological target molecule, a target group having a covalent bonding activity that is modulated (decreased or increased) by binding on the target of a noncovalently driven effector ligand, even without prior structural or functional knowledge of the target or any ligand.

It is also an object of this invention to provide an efficient method for identifying a ligand that acts as a noncovalently driven effector for modulation of a specific covalent bonding activity of a target group on a biological target molecule, without prior structural or functional knowledge of the target or any ligand.

It is a further object of this invention to provide a method for identifying an effector binding site on a target molecule where binding of a noncovalently driven effector modulates specific covalent bonding of a target group, including such binding sites that overlap, adjoin or are distal to the target site comprising the covalent bonding group that is modulated by the effector.

Yet another object of this invention is to provide a method, for a target molecule having a main active site associated with a main ligand binding and/or catalytic activity, to identify effector binding sites distinct from, either proximal or distal to that main active site, where effector binding modulates covalent bonding of a target group that is either part of, distinct from, proximal or distal to that main active site.

Still another object of this invention is to provide a method for mapping modulatory binding sites on biological target molecules, that is, binding sites for effectors that modulate specific covalent bonding of a target group.

These and other objects are provided by the present invention, which is based in part upon an appreciation by the inventor, first, that site-specific modification of biological target molecules, particularly covalent bonding of a selected reactive target group to a functional group linked to a polyalkylene oxide polymer such as polyethylene glycol (PEG), can be facilitated by use of an activated polymer complex comprising a ligand moiety that specifically binds to a target site in or near the selected reactive target group.

In one aspect, the present invention provides a method for modification of a target group in or near a secondary ligand binding site on a biological molecule. The method generally includes the step of contacting a biological molecule with at least one site-specific activated polymer complex, which includes: a functional group reactive with the target group; a polymer linked to the functional group; and a ligand moiety that specifically binds to a secondary ligand binding site. Thus, site-specific covalent bonding of the target group on the biological molecule via the functional group is effected.

In one embodiment, the ligand moiety preferentially binds with the secondary ligand binding site. In one embodiment, the biological molecule comprises a plurality of secondary ligand binding sites, and the ligand moiety binds to only one of the plurality of secondary ligand binding target sites.

In another embodiment, the biological molecule is contacted with the activated polymer complex in the presence of at least one other molecule including at least one other reactive group that covalently bonds to the functional group, and the ligand moiety is selected to avoid binding that would effect covalent bonding of the other reactive group to the functional group linked to said polymer.

In one embodiment, the secondary-site specific ligand moiety is a peptidyl ligand moiety. In one preferred embodiment, the functional group is directly linked to the polymer so that when the functional group becomes covalently linked to the reactive group on the target molecule, the polymer becomes linked via the functional group directly to the reactive group and the peptidyl ligand moiety does not become linked to the target molecule. The activated polymer complex can be, e.g., any of the activated polymer complexes shown in Eqns. 5-7 of FIG. 1B and Eqns. and 9-11 of FIG. 1C.

In another preferred embodiment, the functional group is linked to the polymer via an intervening linker so that when the functional group becomes covalently linked to the reactive group on the target molecule, the polymer becomes covalently linked via the intervening linker and the ligand moiety also becomes linked to the target molecule. The intervening linker can include at least one peptidyl bond of the peptidyl ligand moiety that becomes linked to the target molecule. The activated polymer complex can be, e.g., any of the activated polymer complexes shown in Equations 13-15 of FIG. 1D.

In another preferred embodiment, the intervening linker that links the functional group to the polymer is linked to the peptidyl ligand moiety that becomes linked to the target molecule such that the intervening linker includes no peptidyl bond of the peptidyl ligand moiety. The activated polymer complex can be, e.g., any of the activated polymer complexes in Equation 8 of FIG. 1B and Equation 12 of FIG. 1C.

In one embodiment, the peptidyl ligand moiety is further linked reversibly to a solid support, either directly or via the polymer. In another embodiment, the reactivity of the functional group with the reactive group on the biological molecule is photochemically induced.

In one embodiment, the present invention relates to a method for site-specific modification of a reactive target group in or near a ligand binding target site on a biological molecule, where the site-specific modification comprises covalent bonding of the reactive target group to a functional group linked to a polyalkylene oxide polymer. This method comprises: (a) contacting the biological molecule, under conditions such that the reactive target group covalently bonds to the functional group, with at least one site-specific activated polymer complex. This invention complex comprises: (i) the functional group linked to a polyalkylene oxide polymer and (ii) a ligand moiety that specifically binds to the ligand binding target site, thereby effecting site-specific covalent bonding of the reactive target group on the biological molecule to the functional group linked to a polyalkylene oxide polymer.

In particularly preferred embodiments, the polyalkylene oxide polymer of the activated polymer complex is a polyethylene glycol polymer. In this method the biological molecule may be any biological molecule, but in preferred embodiments, the biological molecule is selected from the group consisting of a peptide, a polypeptide and a protein.

In some embodiments, the biological molecule is contacted with the site-specific activated polymer complex in the presence of at least one test activated polymer complex comprising: (i) the functional group linked to a polyalkylene oxide polymer and (ii) a potential ligand moiety to be tested for specifically binding to the ligand binding target site. In this case, the potential ligand moiety is preferably selected to be different from (non-competitive with) the site-specific ligand moiety.

In other embodiments of the invention method for site-specific modification, the biological molecule comprises more than one reactive target group, each being in or near a different ligand binding target site, and the ligand moiety is selected to bind to only one of the different ligand binding target sites.

In still other embodiments, the biological molecule is contacted with the activated polymer complex in the presence of at least one other molecule comprising at least one other reactive group that covalently bonds to the functional group of the activated polymer complex. In such cases, the ligand moiety of the complex is selected to avoid binding of the ligand moiety that would effect covalent bonding of the at least one other reactive group to the functional group linked to the polyalkylene oxide polymer.

The ligand moiety of the activated polymer complex is preferably a peptidyl ligand moiety, which optionally comprises at least one synthetic amino acid or one surrogate amino acid. For instance, the synthetic amino acid may be selected from the following group: β-alanine, γ-aminobutyrate, O-methyl-substituted threonine, O-methyl-substituted serine, and O-methyl-substituted tyrosine. The surrogate amino acid may be selected from the following group: β-thiazolealanine, β-thiadiazole-alanine, β-isothiazole-alanine, β-isoxazole-alanine, oxazole-alanine, β-benzoxazole-alanine, β-benzisoxazole-alanine, β-benzisothiazoles, β-benzthiazoles, and 2-acylimino-3H-thiazoline derivatives.

In some embodiments of the invention method using a peptidyl ligand moiety, the functional group of the activated polymer complex is directly linked to the polyalkylene oxide polymer so that the polymer becomes linked via the functional group directly to the reactive target group. In these embodiments, the peptidyl ligand moiety does not become linked to the biological molecule. Such embodiments are illustrated, for instance, by the group of activated polymer complexes consisting of those shown in Eqns. 5-7 of FIG. 1B and Eqns. and 9-11 of FIG. 1C.

The functional group of the activated polymer also may be linked to the polyalkylene oxide polymer via an intervening linker so that the polymer becomes linked to the reactive target group via the intervening linker and the ligand moiety also becomes linked to the target. In some cases, the intervening linker that links the functional group to the polymer comprises at least one peptidyl bond of the peptidyl ligand moiety that becomes linked to the biological molecule, as exemplified in the group of activated polymer complexes shown in Equations 13-15 of FIG. 1D. Alternatively, the intervening linker that links the functional group to the polymer is linked to the peptidyl ligand moiety that becomes linked to the biological molecule such that the intervening linker comprises no peptidyl bond of the peptidyl ligand moiety, as in the activated polymer complexes in Equation 8 of FIG. 1B and Equation 12 of FIG. 1C. In any case, the peptidyl ligand moiety may be further linked reversibly to a solid support, either directly or via the polyalkylene oxide polymer.

The functional group linked to a polyalkylene oxide polymer may be any known functional group that is reactive with a reactive group of the target. Preferably, the functional group is selected from the following group: a dithioester; a thioloester; thionoester; a selenoester; a selenoloester; a selenonooester; a phosphonoester; a phosphoric ester; a phosphinic ester: a sulfonate ester; an isocyanate; a diazoester; a diazoketone; diazoamide; an acylphosphate; an imine; a thioimin; an o-salicylate; a p-salicylate; a m-salicylate; a disulfide; an acetylene dicarboxylate dimethyl ester and a half ester or half amide thereof; a fumaric acid or maleic acid and their esters and derivatives thereof; an a-nitroacrylic acid ester; phenylglyoxal; glyoxal; 2,3-butanedione; cyclohexanedione; an $\alpha$-keto- or $\beta$-keto acid or ester; a di- or trifluoromethylketone; a trinitrobenzenesulfonic acid; a tetranitromethane; a diethylpyrocarbonate; an N-bromosuccinimide; a dithiothreitol; a sodium tetrathionate; a 1-ethyl-3-(3-dimethylaminopropyl) carbodiimide; an N-ethoxycarbonyl-2-ethoxy-1,2-dihydroquinoline; a fluoro-2,4-dinitrobenzene; and a (4-aminosulfonyl)-7-fluoro-2,1,3-benzoxadiazole. In some cases, reactivity of the selected functional group of the reactivity probe with reactive target group is photochemically induced, using photoinducible functional groups known and available in the art, as described hereinabove.

In another aspect, the present invention provides an activated polymer complex for secondary site-specific modification of a target group in or near a secondary ligand binding site. The activated polymer complex generally includes a functional group potentially reactive with the target group, a polymer linked to the functional group, and a secondary site-specific ligand moiety. The activated polymer complex can be used, for instance, in the above invention method for site-specific modification of a biological target molecule.

In one embodiment, the secondary-site specific ligand moiety is a peptidyl ligand moiety. In one preferred embodiment, the functional group is directly linked to the polymer so that when the functional group becomes covalently linked to the reactive group on the target molecule, the polymer becomes linked via the functional group directly to the reactive group and the peptidyl ligand moiety does not become linked to the target molecule. The activated polymer complex can be, e.g., any of the activated polymer complexes shown in Eqns. 5-7 of FIG. 1B and Eqns. and 9-11 of FIG. 1C.

In another preferred embodiment, the functional group is linked to the polymer via an intervening linker so that when the functional group becomes covalently linked to the reactive group on the target molecule, the polymer becomes covalently linked via the intervening linker and the ligand moiety also becomes linked to the target molecule. The intervening linker can include at least one peptidyl bond of the peptidyl ligand moiety that becomes linked to the target molecule. The activated polymer complex can be, e.g., any of the activated polymer complexes shown in Equations 13-15 of FIG. 1D.

In another preferred embodiment, the intervening linker that links the functional group to the polymer is linked to the peptidyl ligand moiety that becomes linked to the target molecule such that the intervening linker includes no peptidyl bond of the peptidyl ligand moiety. The activated polymer complex can be, e.g., any of the activated polymer complexes in Equation 8 of FIG. 1B and Equation 12 of FIG. 1C.

In one embodiment, the peptidyl ligand moiety is further linked reversibly to a solid support, either directly or via the polymer. In another embodiment, the reactivity of the functional group with the reactive group on the biological molecule is photochemically induced.

In one embodiment, the complex comprises: (i) a functional group linked to a polyalkylene oxide polymer and (ii) a peptidyl ligand moiety. The functional group of the activated polymer complex may be directly linked to the polyalkylene oxide polymer, as described above and illustrated by the complexes shown in Eqns. 5-7 of FIG. 1B and Eqns. and 9-11 of FIG. 1C. Alternatively, the functional group may be linked to the polyalkylene oxide polymer via an intervening linker, as described above, and the intervening linker may comprise at least one peptidyl bond of the peptidyl ligand moiety that becomes linked to the target molecule, as in Equations 13-15 of FIG. 1D. In other cases, the intervening linker is linked to said peptidyl ligand moiety such that said intervening linker comprises no peptidyl bond of said peptidyl ligand moiety, as illustrated in Equation 8 of FIG. 1B and Equation 12 of FIG. 1C. In any embodiment the activated polymer complex of the invention may have a peptidyl ligand moiety that is further linked reversibly to a solid support, either directly or via the polyalkylene oxide polymer.

In yet another aspect, the present invention provides a method for identifying an activated polymer complex for secondary site-specific modification of a target group in or near a secondary ligand binding site. The method includes the step of contacting a biological molecule with a library of activated polymer complexes, each activated polymer complex including a functional group potentially reactive with the target group, a polymer linked to the functional group, and a secondary site-specific ligand moiety. The method also includes the step of identifying an activated polymer complex that modifies a target group and binds with specificity to a secondary ligand binding site.

In one embodiment, the method includes the step of determining whether the activated polymer complex affects the primary activity of the biological molecule, e.g., whether the activated polymer complex inhibits or enhances the primary activity of the biological molecule. In another embodiment, the invention includes the step of determining the rate of modification by quenching the reaction at a predetermined time and measuring the amount of modification. In another embodiment, the method includes the step of at least partially digesting the biological molecule to determine the position of attachment of an activated polymer complex.

In another aspect, the invention provides a method for identifying a competitive site-specific activated polymer complex comprising the step of: identifying a second activated polymer complex for secondary site-specific modification of the target group in or near the secondary ligand binding site using the above method.

Others of the above stated objects are provided by the present invention, based in part upon an appreciation by the inventor that tandem analyses of covalent bonding of reactive groups and noncovalent binding of potential ligands, combined, can provide diversity of drug leads by systematically identifying specific covalent bonding activities of a biological target molecule that are modulated by binding of an effector ligand to the target-even without previous structural or functional knowledge of the target or a reactive group thereon. More precisely, the invention methods identify and map ligand binding sites that are either nonmodulatory, where occupancy has no effect, or modulatory, where noncovalently driven effector binding modulates stable covalent bonding of a specific reactive target group and, preferably, correlated enzymatic or binding target activity. Thus, identification of diverse unmodulated and modulated target reactivities and effectors related to the latter enables site-specific covalent bonding of an adduct, such as PEG or a drug, to different target locations, thereby offering diverse defined leads for functional analyses of specific modifications.

Alternatively, or in addition, identifying different modulated target reactivities enables design of distinct effectors, optimized for binding to structurally and functionally distinct target sites, which therefore offer multiple chemically and pharmacologically diverse candidates for development of multiple, wholly different, small molecule drugs for each selected target molecule.

For a target having a known main activity that resides at a main "active site", systematically identifying and exploiting different modulated reactive target groups also promotes drug lead diversity by avoiding inherent biases in other approaches that limit drug lead diversity. Thus, as noted above, screens that test for drug effects only on one known function of a target (e.g., an enzymatic or receptor activity) are precluded by design from identifying other potentially useful drug effect(s), on target activities that are independent of the main activity and its related main active site. These undetected ligand binding effects may enable selective control, for instance, of potentially desirable chemical alterations so as to minimize affects on the main active site and/or distinct sites that mediate interaction(s) with other cellular components, such as regulatory proteins or nucleotide messengers.

Systematically identifying multiple distinct modulated reactive target groups, according to the present invention, also avoids a further known structural bias inherent in any approach in which only one known function of a target, particularly noncovalent binding of a ligand, determines specificity of interactions with potential drugs. As discussed above, all such approaches are most likely to detect ligands that bind only to the main active site, because that main active site is typically "stickier" than any other target site. (See, e.g., Ruppert, et al. *Protein Sci.*, 6, 524-533 (1997)) In contrast to such conventional screening strategies, the invention method simply does not respond to, and hence does not identify as a drug lead, any ligand that does not affect a specifically monitored covalent reactivity of the selected target group(s); ligands that exclusively bind to the main active site, or any other site that is "stickier" than those having desired modulatory effects, simply are not recognized as effectors, or even as ligands of the target, unless binding at the stickier site also modulates monitored specific bonding of selected target group(s).

Furthermore, the present invention detects even effectors that bind only weakly to a modulatory site for a monitored reactivity, despite the presence of ligands that bind more tightly to other binding sites that lack such specific modulatory effect. While some known drug screens that use affinity labels also may allow identification of weakly binding ligands, those approaches still suffer bias, not only from the above mentioned dominant stickiness of a main active site, but also from limited choices of chemistries and geometries for coupling reactive group probes to binding moieties of affinity labels. Thus, the constraints on a reactive group, both chemical and steric, to enable a reactive group to specifically bond with both a reactive target group and a ligand moiety of the labeling molecule, significantly reduce the functional and structural diversity of the affinity label as a whole. In particular, testing only one specific configuration of a functional group linked to a given binding moiety, as is usually done with affinity label libraries, markedly restricts the diversity of geometric relationships between target bonding and binding groups that can be detected, compared to the much broader diversity that could be detected using the same affinity label components in multiple diverse configurations.

Accordingly, the present invention is further grounded on an understanding by the inventor that to optimize drug lead diversity by systematically identifying reactive target groups, and particularly, modulated reactivities thereof, requires the use of physically separate reactive groups and potential ligands to independently probe target reactivity and effector binding, thereby optimizing geometric diversity of target bonding and binding groups that can be detected by a given combination of reactive group and potential ligand. Thus, using physically independent probes for bonding and binding on a selected target, according to the present invention, enables identification of modulated activities and related effectors, regardless of the spatial relationship between reactive target groups and sites of related effector binding, that is, whether a modulated reactive group lies at, near, or far from a related effector binding site.

In addition, use of separate probes for reactive target group bonding and ligand binding, as in this invention, eliminates yet another bias common to all methods of screening affinity labels, including "tethered" ligands, whereby such assays generally do not detect ligands that modulate, particularly inhibit, reactivity of the reactive target group that covalently directs an affinity label to a selected site. Moreover, preselection of a reactive target group and site for tethering, particularly in or near a main active site, and especially selection of a genetically engineered tethering group (See, e.g., patent documents of Erlanson et al.) generally presupposes knowledge of what sites are useful for ligand binding. This in turn presupposes substantial understanding of target structure and function. Otherwise, using tethered ligands to identify potentially useful ligand binding sites would require costly testing of multiple artificial tethering groups, generated at random sites. Further, binding sites identified by genetically engineered tethering may exhibit important differences in binding specificity and/or other functions compared to the native structure that ultimately is the desired target for most drugs.

In contrast to known affinity labeling approaches, however, including tethering, the present invention is readily applied to any target molecule without prior structural or functional knowledge of the target, its main active site, or any ligand, to identify specific reactivities of the native structure that are usefully modulated by effectors binding to that structure, by any regulatory mechanism, whether competitive or allosterically (or otherwise) noncompetitive.

Systematic identification of modulatable target reactivities on any biological molecule, with or without prior structural or functional information, using separate bonding and binding probes according to the present invention, is readily carried out with tandem bonding and binding assays that employ already available technologies. Thus, chemically and topologically diverse reactive target groups that are accessible for covalent bonding with various group-specific probes are readily identified (and physically mapped) on a polypeptide, for instance, using known methods for selective chemical modification. For example, Krell et al., *J. Pept Res.*, 51, 3, 201-209 (1998) and Wells, et al. PCT Publication No. WO 00/00823 and corresponding U.S. Pat. No. 6,335,155B1, describe such methods that use known selective reagents and electrospray mass spectrometry for monitoring the extent and location(s) of various modifications. Any covalent bonding activity between a group-specific probe and a particular reactive target group that is so identified (and mapped) can then be assayed in the presence of diverse potential ligands to determine whether this particular target group activity is modulatable by an effector ligand. Alternatively, a target group having a specific covalent bonding activity that is specifically stimulated or activated by an effector also can be identified by tandem assays of this invention, by looking for covalent bonding of a reactive group probe that increases, or occurs at all, only when a particular potential ligand is present. In any case the invention identifies modulatable target group reactivities by detecting some change (increase or decrease) in specific covalent bonding of a particular target group that correlates with specific binding of a particular potential ligand, using physically separate probes for bonding and binding activities. In its most general form, using minimally sized reactive molecules that are capable of specific or selective probing of different covalent bonding chemistries, and optimally diverse potential ligand structures (absent only those that would covalently bond with a concurrently tested functional group of a reactivity probe), the invention theoretically allows identification of any effector ligand that modulates a covalent bonding activity of any selected reactive target group. This is true regardless of where the effector binding site lies—at, near or far from either the modulated group or the main (stickiest) active site of the target. It should be noted, however, that either or both of the reactivity and binding probe components of this invention may be selected to function as an affinity label, that is, to form specific combinations with the target molecule that are driven by both covalent and non-covalent interactions, so long as the reactivity probe is not physically associated (covalently or noncovalently) with the binding probe (potential ligand) under conditions of testing for effectors that modulate target group reactivity.

In any event, the invention method is able to identify a modulatable activity of a biological molecule, particularly a covalent bonding activity, and an effector ligand that modulates (e.g., inhibits, stimulates or activates) that activity, regardless of whether the modulatory ligand binds at, near or distal to a reactive target group having a covalent bonding activity selected for monitoring. For example, the invention can detect an effector that inhibits target group reactivity by directly blocking access of that reactive group to the covalent bonding (reactivity) probe. Alternatively, detected effector ligands that modulate a monitored target group may bind to a site distal to that reactive group and still affect the monitored activity, such as by an allosteric mechanism that may cause, for instance, (1) reduced activity due to occlusion of access or some other microenvironmental alteration affecting a target group or some "cofactor" needed for a monitored activity; or (2) increased activity, due to exposure of an inaccessible target group or some other reactivity enhancing alteration.

Embodiments of the invention that employ potential ligands lacking an attached functional group also reduce the amount and complexity of chemistry needed to prepare ligand libraries, compared to using affinity labels as potential ligands. Thus, the same ligand library can be tested for effects on covalent reactivity of chemically different classes of reactive target groups, so long as the potential ligands do not covalently react with a selected reactivity probe used to detect covalent bonding of a target group. On the other hand, embodiments that use affinity labels as potential ligands also can identify effectors, particularly weakly binding ligands, that modulate specific target group activity, regardless of where on the target the modulatory affinity label binds and bonds, so long as target group reactivity is monitored with a reactivity probe that is physically separate from and, preferably, unreactive with, the screened affinity labeling ligands.

In yet another aspect, the invention provides a method for selecting a secondary-site specific effector molecule including the steps of: (a) identifying one or more secondary-site specific molecules that modulate stable covalent bonding of a reactivity probe with a target group in or near a secondary ligand binding site on a biological molecule; and (b) selecting a secondary-site specific molecule that effects a primary binding site activity of the biological molecule, wherein said secondary-site specific molecule is a secondary-site specific effector molecule.

In one embodiment, step (a) includes determining the extent of specific binding of one or more test molecules, e.g., using NMR spectroscopy or X-ray crystallography. In another embodiment, step (a) also includes determining the difference in the extent of stable covalent bonding in the absence and presence of said test molecule. In one embodiment, the reactivity probe comprises a leaving group that is displaced upon covalent bonding with the biological molecule, and the difference in the extent of stable covalent in the absence and presence of said test molecule is the difference in the amount of leaving group displaced in the present and the absence of said test molecule. In another embodiment, a correlation between the extent of specific binding of a test molecule to the biological molecule, and a difference in the extent of stable covalent in the absence and presence of said test molecule, identifies a molecule as a secondary-site specific molecule.

In certain embodiments, the primary binding site activity is an enzymatic activity, antibody binding activity, or a receptor binding activity. The secondary site-specific molecule may or may not block primary binding site activity.

Another aspect of the invention includes a method of selecting a secondary-site specific inhibitor molecule that includes the steps of: selecting one or more secondary-site specific effector molecules according to the above method; and selecting a secondary-site specific effector molecule that inhibits the primary binding site activity, wherein said secondary-site specific effector molecule is a secondary-site specific inhibitor molecule.

In one embodiment, the method includes determining whether the inhibitor is a competitive inhibitor or a noncompetitive or uncompetitive inhibitor.

In another embodiment, the effector molecule further comprises a second functional group. The second functional group can effect stable covalent bonding with an anchor group on the biological molecule. In some embodiments, the effector molecule is a small organic compound or a peptidyl ligand moiety or a carbohydrate ligand moiety.

In another aspect, the invention provides a secondary-site specific effector molecule identified by a method according to the above methods of selecting the same. In yet another aspect, the invention provides a library of secondary-site specific effector molecules identified by a method according to the above methods of selecting the same.

In yet another aspect, the invention provides a method for modulating secondary site-specific modification of a biological molecule that includes the step of contacting the biological molecule with a secondary-site specific effector molecule identified according to the above methods. The primary binding site activity can be an enzymatic activity, antibody binding activity, or a receptor binding activity. The secondary site-specific molecule can, in some embodiments, inhibit or block primary binding site activity.

Another major aspect of the present invention, therefore, relates to a method for identifying an effector molecule that modulates a target activity of a biological molecule by specific binding to an effector binding target site on the biological molecule. This target activity comprises at least stable covalent bonding of a reactive target group on the biological molecule with a selected functional group. In this invention method, preferably the biological molecule is a peptide, a polypeptide or a protein selected from the group consisting of: an enzyme, a receptor, an antibody, a hormone, a cytokine and a functional fragment of an enzyme, a receptor, an antibody, a hormone or a cytokine.

This invention method comprises the following steps. Step (a) is contacting the biological molecule with a first molecule that is a reactivity probe comprising the selected functional group, in the absence and presence of a second molecule that is a potential ligand of the biological molecule. This contacting is performed under test conditions where the stable covalent bonding of the target reactive group is detected, either in the absence of, or presence of, the potential ligand (or at different levels in the absence and presence of the potential ligand). Step (b) is determining under the same test conditions, in the absence and presence of the potential ligand, the extent, if any, of the stable covalent bonding being monitored with the reactivity probe. Step (c) involves determining under those same test conditions, in the presence of the potential ligand, the extent, if any, of specific binding of the potential ligand to the biological molecule.

In this method, a difference between the extent of the stable covalent bonding monitored with the reactivity probe, in the absence and presence of the potential ligand, that correlates with the extent of specific binding of the potential ligand, indicates that the potential ligand is an effector molecule. In particular, such a difference in covalent bonding extent indicates that the identified effector molecule modulates stable covalent bonding of the reactive target group by specific binding to an effector binding target site on the biological molecule.

Preferably, in this method, the target activity of that biological molecule, that comprises at least stable covalent bonding of a reactive target group on the biological molecule with a selected functional group, further comprises an enzymatic target activity or a specific binding target activity that correlates with the stable covalent bonding of the target reactive group with the selected functional group of the reactivity probe. For instance, the specific binding target activity may comprise a receptor binding activity of the biological molecule.

In some embodiments of the invention method, the difference between the extent of the monitored stable covalent bonding in the absence and presence of the potential ligand is a decrease in the extent of that covalent bonding that correlates with the extent of specific binding of said potential ligand. Such correlating decreases indicate that the potential ligand is an effector molecule that is an inhibitor of the stable covalent bonding of the reactive target group. In some such cases, the reactive target group that is inhibited is in or near a ligand binding target site and the reactivity probe comprises a ligand moiety that specifically binds to that ligand binding target site.

Optionally, the invention method further comprises determining whether an inhibitor of said stable covalent bonding activity is (a) a competitive inhibitor or (b) a noncompetitive or uncompetitive inhibitor, which may be determined, for instance, by determining whether binding of the inhibitor to the effector binding target site inhibits binding of the ligand moiety to the ligand binding target site. In this case, binding of the inhibitor that inhibits the binding of the ligand moiety indicates that the inhibitor is a competitive inhibitor of the stable covalent bonding activity, and binding of the inhibitor that does not inhibit the binding of the ligand moiety indicates that the inhibitor is either a noncompetitive inhibitor or an uncompetitive inhibitor of the stable covalent bonding activity. Alternatively, determining whether the inhibitor of the stable covalent bonding activity is a competitive or, on the other hand, a noncompetitive or uncompetitive inhibitor is determined by kinetic analyses, preferably by determining whether excess reactivity probe immediately overcomes inhibition by the inhibitor. If excess reactivity probe (analogous to an enzyme substrate) immediately overcomes inhibition by the inhibitor, this indicates that the inhibitor is a competitive inhibitor of the stable covalent bonding activity. Where excess reactivity probe does not immediately overcome inhibition by the inhibitor, the inhibitor is either a noncompetitive inhibitor or an uncompetitive inhibitor of the stable covalent bonding activity. These two types of inhibitors may be further distinguished by further conventional kinetic and structural analyses. Thus, the invention method optionally further comprises, when the inhibitor is not a competitive inhibitor of the stable covalent bonding activity, determining whether the inhibitor is a noncompetitive or uncompetitive inhibitor, by determining whether binding of the inhibitor to the effector binding target site requires binding of the ligand moiety to the ligand binding target site. In this case, binding of the inhibitor that does not require binding of the ligand moiety indicates that the inhibitor is a noncompetitive inhibitor, and binding of that inhibitor that does require binding of the ligand moiety indicates that the inhibitor is an uncompetitive inhibitor.

When an inhibitor is found to be a competitive inhibitor of the stable covalent bonding activity, the method optionally further comprises a determining whether the competitive inhibitor is a classical or nonclassical competitive inhibitor, for instance, by determining whether the inhibitor binds to an effector binding target site that overlaps with the ligand binding target site. Here, an effector binding target site that overlaps the ligand binding target site indicates that the competitive inhibitor is a classical competitive inhibitor, and an effector binding target site that does not overlap the ligand binding target site indicates that the competitive inhibitor is a nonclassical competitive inhibitor.

In some instances of applying the above invention method, the difference between the extent of stable covalent bonding in the absence and presence of a potential ligand is an increase in the extent of the covalent bonding that correlates with the extent of specific binding of the potential ligand. This indicates that the potential ligand is an effector molecule that stimulates the monitored stable covalent bonding of the reactive target group. If the monitored stable covalent bonding that increases does not occur at a detectable level in the absence of the potential ligand, this indicates that the potential ligand is an effector molecule that activates the stable covalent bonding of a normally unreactive target group.

In some cases, the biological molecule may comprise a reactive anchor group in or near the effector binding target site. In such cases, the potential ligand is advantageously an affinity label further comprising a second selected functional group operably linked to the potential ligand such that specific binding of the potential ligand to the effector binding target site affects stable covalent bonding of the reactive anchor group with the second selected functional group of the affinity label. Preferably, the second selected functional group that is on the affinity label is different from the (first) selected functional group of the reactivity probe, and the second functional group is selected so that the reactive target group does not covalently bond with the second functional group on the affinity label.

The potential ligand used in the invention methods may be a small organic compound or advantageously may comprise, for instance, a peptidyl ligand moiety, or a carbohydrate ligand moiety.

In another aspect, the invention provides an effector molecule that modulates a target activity of a biological molecule by specific binding to an effector binding target site on that biological molecule, where the target activity comprises at least stable covalent bonding of a reactive target group on the biological molecule with a selected functional group, where the effector molecule is identified by the above method of the invention.

Yet another aspect of the invention provides a method for modulating site-specific modification of a reactive target group in or near a ligand binding group on a biological molecule. This site-specific modification comprises at least covalent bonding of the reactive target group to a functional group linked to an adduct moiety. The effector molecule used in this method is an effector molecule identified by the above invention method for identifying such effectors. In this method for modulating site-specific modification, the effector modulates covalent bonding of the reactive target group by specific binding to an effector binding target site, thereby modulating the covalent bonding of the reactive target group with the functional group linked to the adduct moiety. Further, in this method the biological molecule is advantageously a peptide, a polypeptide or a protein, and the adduct comprises a polyalkylene oxide polymer. Alternatively, the adduct may comprise a macromolecule having a biological function, such as a targeting function. The macromolecule that comprises a targeting function is selected, for instance, from the group consisting of an antibody, an antigen-binding fragment of an antibody, a soluble receptor, and a soluble ligand binding fragment of a receptor.

In yet another aspect, the invention provides a method for modulatory mapping of a biological molecule that includes the step of contacting a biological molecule with a reactivity probe, which includes a ligand moiety that specifically binds to a secondary ligand binding site on a biological molecule, and a functional group reactive with a target group in or near the secondary site, thereby effecting site-specific covalent bonding of the target group on the biological molecule via the functional group. The method further comprises the step of mapping the secondary ligand binding site and the target group in or near the secondary ligand binding site on the biological molecule.

In yet another aspect, the invention provides a method for obtaining a map of secondary ligand binding sites and target group sites in or near the secondary ligand binding sites on a biological molecule that includes mapping a plurality of secondary ligand binding sites and target groups on a molecule according to the above method for modulatory mapping.

In one embodiment, the method includes mapping whether the reactivity probe effects a primary binding site activity of the biological molecule and mapping the effect, if any, of the secondary ligand binding site on the primary binding site activity.

Additionally or alternatively, the method can include mapping primary binding site activity, e.g., enzymatic activity, a receptor binding activity, or an antibody binding site.

Yet another aspect of the invention is a method for modulatory mapping of target activities of protein sites. This method comprises making a representational map identifying (i) at least one activity target site comprising a reactive target group and (ii) at least one effector binding target site having a modulatory effect on the target activity site. Steps of this method comprise: (a) identifying an effector molecule that modulates a target activity of the protein by specific binding to an effector binding target site on the protein. This target activity comprises at least stable covalent bonding of the reactive target group with a selected functional group. Identifying such an effector molecule is carried out by the invention method above. Step (b) of the modulatory mapping method of the invention involves mapping on the representational map the target activity site comprising the reactive target group, whereas step (c) involves mapping on that same representational map the effector binding target site. Preferably, this mapping method further comprises a step of mapping on the representational map a ligand binding target site, if any, that the reactive target group is in or near, having a specific binding target activity that the effector molecule modulates by specific binding to the effector binding target site. This method also may comprise mapping on the representational map a catalytic activity target site, if any, that the reactive target group is in or near, having a catalytic target activity that the effector molecule modulates by specific binding to said effector binding target site. The method may further comprise mapping on the representational map an antibody binding site, preferably an antibody that is an effector molecule that modulates a target activity of the biological molecule.

For instance, the invention method will identify cases where the biological molecule is a protein and the useful activity that is modulated by the identified effector molecule is an enzymatic activity of that protein. This enzymatic activity may require the modulated target group to covalently bond to a substrate or cofactor for that enzymatic activity. Accordingly, the potential ligand may inhibit the enzymatic activity by steric hindering of covalent bonding of said target group to the substrate or cofactor, or by allosteric hindering of the covalent bonding of the target group to the substrate or cofactor.

The invention method also may identify a usefully modulatable target activity that is a binding activity specific for a functional ligand other than the potential ligand that acts as an effector. In some cases, this specific binding activity may require direct noncovalent interaction of the reactive target group with the other functional ligand, and the potential ligand inhibits that specific binding activity by steric hindering of that direct noncovalent interaction. Alternatively, the potential ligand may be one that inhibits the specific binding activity by allosteric hindering of the direct noncovalent interaction of the reactive target group and functional ligand.

In the above invention methods, the modulatable activity comprises stable covalent bonding of a reactive target group on the biological molecule with a selected functional group. The term "stable" covalent bonding means that the bonding is sufficiently stable to permit manipulations of the biological molecule necessary to determine where the covalently bonded target group is located, e.g., stable to denaturation and/or mass spectrophotometric analyses. In this context, stable covalent bonding would not include, for instance, a situation like that discussed in Stout et al., *Structure* 6, 839-848 (1998), where binding of a specific coenzyme analog was found to "trap" a substrate in an "isolatable" covalent linkage with a catalytic thiol group of the protein via a slow isomerization, providing a ternary complex that can be isolated on nitrocellulose membranes or by gel filtration, but treatment of the complex with sodium dodecyl sulfate ($NaDodSO_4$), which would denature the protein but not disrupt stable covalent bonds according to this invention, results in the dissociation of both ligands in an unmodified form.

According to teachings of this invention, in the method for identifying effectors, the reactivity probe (comprising the functional group) and the potential ligand are physically separate molecules, to independently probe target reactivity and effector binding. Contacting the biological molecule with a reactivity probe and potential ligand is performed under test conditions such that the stable covalent bonding of a target group with the probe is detectable, either in the presence of the potential ligand or in the absence of that potential ligand, or both. Thus, the covalent bonding of a target group to a probe might occur only when the potential ligand is absent, or only when it is present, or it might occur when that ligand is present and when it is absent, but at different levels.

After contacting the biological molecule, reactivity probe and potential ligand under the necessary conditions, the next step is determining, in the presence and absence of the potential ligand, the extent, if any, of the stable covalent bonding to the probe. For instance, this can be determined by any of a variety of methods known in the art for detecting chemical modification of a biological molecule, such as the mass spectrophotometric methods of Krell et al., supra. The next step in identifying effectors involves determining under the same test conditions used for determining covalent bonding, with the potential ligand present, the extent, if any, of specific binding of the potential ligand to the biological molecule. Specific binding of two molecules can be detected by a variety of methods known in the art, for instance, by separating unbound ligand and biological molecule by attachment of one or the other to a solid phase support which is washed to remove unbound components. In addition, where the potential ligand is an affinity ligand or a tethered ligand, whereby ligand binding facilitates specific covalent bonding to the biological molecule, then binding of potential ligand also can be determined by including an indirectly detectable label on the potential ligand (such as fluorescent or radioactive label or biotin), or also by direct detection of modification of the mass of the biological molecule.

The order of step (c) (determining the extent, if any, of specific binding of a potential ligand to the biological molecule), with respect to step (b) (determining, in the presence and absence of the potential ligand, the extent, if any, of the stable covalent bonding to the probe) is not critical, so long as steps (b) and (c) are performed under the same test conditions. Thus, one may first test potential ligands for an ability to bind to the biological molecule under the proper test conditions, as in step (c), and then determine effects of proven ligands on covalent bonding of a target group, as in step (b), using the same conditions for both binding and bonding tests.

In this invention method for identifying an effector molecule that modulates a target activity, a difference between the extent of stable bonding to the probe in the presence of a potential ligand and the extent of stable bonding in the absence of that potential ligand, determined in step (b), may be used to a particular potential ligand is an effector molecule that modulates the monitored stable covalent bonding by specific binding to the biological molecule. Alternatively, one of ordinary skill would readily appreciate that testing potential ligands for effects on covalent bonding activity of a target group may be done in the presence of a potential ligand at two or more different concentrations, by determining whether and what different levels of covalent bonding occur with those different concentrations of the potential ligand. Again, a difference between the extent of stable bonding to the probe at different concentrations of potential ligand that correlates with the extent of specific binding of that potential ligand at those different concentrations would indicate that a particular potential ligand is an effector molecule for this stable covalent bonding activity.

In preferred embodiments, the invention method for identifying an effector that modulates a target activity includes contacting the biological molecule with a probe in the presence and absence of a mixture of at least three potential ligands, that is to say, with a library of potential ligands, such as an oligomeric or other ligand library. Alternatively, the testing may be done with various subgroups or "pools" or multiple ligand library members.

In another embodiment, this method further comprises a step of determining the location on the biological molecule of the reactive target group, for instance by mass detection methods as in Krell et al supra. Likewise, optionally the method includes a step of determining the location on the biological molecule of specific binding of a potential ligand that is an effector molecule for stable covalent bonding of the reactive target group.

In embodiments of the invention method that comprise mapping of antibody binding sites, the may be done using conventional methods, including, for instance, contacting the biological molecule with an antibody in the presence and absence of a potential ligand, under test conditions such that the antibody specifically binds to the biological molecule in the presence or absence of the potential ligand; determining under those test conditions in the presence and absence of the potential ligand, the extent, if any, to which the antibody specifically binds to the biological molecule; and determining under those test conditions with the potential ligand present, the extent, if any, of specific binding of the potential ligand to the biological molecule. In this method, a difference between the extent to which the antibody specifically binds to the biological molecule in the presence of the potential ligand and the extent to which the antibody specifically binds in the absence of the potential ligand, that correlates with the extent of specific binding of the potential ligand, indicates that specific binding of that antibody is a modulatable activity of the biological molecule that is modulated by binding of the potential ligand. Preferably, this method also includes determining the location(s) on the biological molecule of the specific binding of the antibody and of the specific binding of the potential ligand that is an effector molecule that modulates the specific binding of the antibody.

In any case where an affinity labeling molecule is used as a reactivity probe or potential ligand of the invention, that molecule conveniently comprises a label, such as biotin, a fluorescent moiety or a radioactive moiety, that is used for determining the amount of the probe or potential ligand that specifically bonds and binds to the biological target molecule.

Various molecules suitable as group-specific or group-selective probes for target groups, according to the invention, are known in the art. For instance, Krell et al. reports the use of phenylglyoxal, trinitrobenzene sulfonic acid, tetranitromethane and diethylpyrocarbonate to identify functional amino acid residues, particularly arginine, lysine, tyrosine (and, to a lesser extent, histidine, methionine and tryptophan), and histidine (and cysteine, tyrosine and primary amino groups), respectively. Many more group-specific or group-selective reagents are known and/or disclosed herein (see below).

U.S. Pat. No. 6,277,583B1 to Krantz et al. also discloses affinity labeling libraries with group-specific or group-selective reactive groups that are suitable for use in the practice of the present invention. Similarly, Wells et al., supra, discloses a type of affinity labeling molecule that is suitable for use as a reactive group probe of the present invention, namely, small organic molecule "ligands" for binding to biological target molecules. The binding affinity of these ligands relates to the ability of the compounds to form covalent bonds with a chemically reactive group at the binding site on the target. Preferred libraries of organic compounds disclosed in Wells et al. that are suitable for use herein, comprise aldehydes, ketones, primary amines, secondary amines, alcohols, thioesters, disulfides, carboxylic acids, acetals, anilines, diols, amino alcohols and/or epoxides.

The reactive groups of Krell et al. and Wells et al., however, generally are not reactive with accessible carbon atoms of biological molecules, such as polypeptides, but such groups can be probed, for instance, with a reactive group that is photochemically induced. For instance, affinity labels comprising such photoreactive groups are disclosed in U.S. Pat. No. 5,763,177, to Gold et al. which discloses a method for identifying nucleic acid ligands to target molecules using a method called "SELEX" (Selective Evolution of Ligands by Exponential Enrichment), where the candidate nucleic acids include photoreactive groups. U.S. Pat. No. 5,827,073, to Luescher et al. also discloses photoreactive peptide derivatives suitable for adapting to use as reactive group probes according to the present invention.

Similarly, potential ligands tested in the invention may include molecules of various sizes and chemistries, such as small organic compounds, nucleic acid molecules, carbohydrates and peptides or polypeptides, to name but a few.

Potential ligands to be tested in a mixture, with different reactive group probes, preferably are spatially separated, such as by being bound to solid-phase supports, for convenient separation of unbound and unbonded components from those that are bound and/or bonded. Conveniently, the extent of covalent bonding of the biological molecule to a selected reactive group bound to a solid phase support is determined using an immunoassay to detect bonded biological molecule. Alternatively, the extent of covalent bonding is measured by detecting an increase in the mass of the biological molecule or a fragment thereof, as by mass spectrophotometric means.

Site-specific modifications that may be controlled according to methods of this invention include, for instance, modifications comprising conjugating an adduct to the biological molecule. For example, the biological molecule may be a protein and the specific modification may comprise conjugating polyethylene glycol to the protein, or coupling the protein to another macromolecule having a biological function such as a targeting function. The macromolecule that comprises a targeting function may be, for instance, an antibody, an antigen-binding fragment of an antibody, a soluble receptor, or a soluble ligand binding fragment of a receptor. Functionally speaking, the biological molecule for which modification is to be controlled by the invention method may be a peptide, polypeptide or protein such as an enzyme, a receptor, an antibody, a hormone, a cytokine, a chemokine, or a functional fragment of any of these peptides or polypeptides.

More generally, the invention methods are relevant to any molecule in which it is necessary to differentiate among functional groups of the same type which are located in different environments. In addition to proteins and peptides, these may be carbohydrates, oligonucleotides, antisense molecules, or organic molecules. Specific examples of PEGylated molecules of clinical interest, for instance, include interferons, interleukins, various decoy receptors such TNF-a receptor, various monoclonal antibodies, and various small molecules that possess short duration of action whose lifetimes or immunogenicity can be altered favorably by attachment to PEG.

In yet another aspect, the present invention provides a modified biological molecule that includes a biological molecule having a target group covalently bonded via a functional group to a polymer, wherein the target group is in or near a secondary ligand binding site.

In one embodiment, the molecule includes a ligand moiety bound to the secondary ligand binding site. Optionally, the ligand moiety is linked to the polymer.

The ligand moiety can be a peptidyl ligand moiety that includes, e.g., at least one synthetic amino acid or one surrogate amino acid. The synthetic amino acid or one surrogate amino acid can be any of the same described herein.

In one embodiment, the site-specific modification increases the safety or the efficacy of the biological molecule as compared to an unmodified biological molecule.

In another embodiment, the site-specific modification increases the dosing period of the biological molecule as compared to an unmodified biological molecule, e.g., wherein the dosing period is at least doubled as compared to an unmodified biological molecule. The site-specific modification optionally can reduce or mask an immune response in an organism as compared to an unmodified biological molecule. The site-specific modification can shield antigenic and/or immunogenic epitopes, shield receptor-mediated uptake by RES, prevent degradation by proteolytic enzymes, reduce renal filtration, and alter biodistribution of the biological molecules.

The polymer employed in any of the methods, complexes and the like of the present invention, can be a polyalkylene oxide polymer, a polynucleotide, a protected polypeptide, a polysaccharide. The polyalkylene oxide polymer can be, but is not limited to, a polyethylene glycol polymer, a biotinylated polyethylene glycol polymer, and a fluorescent polyethylene glycol polymer.

The biological molecule employed in any of the inventive methods, complexes and the like, can be a peptide, a polypeptide, a protein, an enzyme, a receptor, an antibody, a hormone, a cytokine, or functional fragments thereof.

The functional group employed in any of the inventive methods, complexes and the like, can be selected from the group consisting of: a dithioester; a thioloester; a thionoester; a selenoester; a selenoloester; a selenonooester; a phosphonoester; a phosphoric ester; a phosphinic ester; a sulfonate ester; an isocyanate; a diazoester; a diazoketone; a diazoamide; an acylphosphate; an imine; a thioimin; an o-salicylate; a p-salicylate; a m-salicylate; a disulfide; an acetylene dicarboxylate dimethyl ester and/or a half ester or half amide thereof; a fumaric acid or maleic acid and their esters and derivatives thereof; an α-nitroacrylic acid ester; a phenylglyoxal; a glyoxal; a 2,3-butanedione; a cyclohexanedione; an α-keto- or α-keto acid or ester; a di- or tri-fluoromethylketone; a trinitrobenzenesulfonic acid; a tetranitromethane; a diethylpyrocarbonate; a N-bromosuccinimide; a dithiothreitol; sodium tetrathionate; a 1-ethyl-3-(3-dimethylaminopropyl) carbodiimide; a N-ethoxycarbonyl-2-ethoxy-1,2-dihydroquinoline; a fluoro-2,4-dinitrobenzene; and a (4-aminosulfonyl)-7-fluoro-2,1,3-benzoxadiazole.

The peptidyl ligand moiety employed in any of the inventive methods, complexes and the like, can include at least one synthetic amino acid or one surrogate amino acid. The synthetic amino acid can be, e.g., β-alanine, γ-aminobutyrate, O-methyl-substituted threonine, O-methyl-substituted serine, or O-methyl-substituted tyrosine. The surrogate amino acid can be, e.g., β-thiazolealanine, β-thiadiazole-alanine, β-isothiazole-alanine, β-isoxazole-alanine, oxazole-alanine, β-benzoxazole-alanine, β-benzisoxazole-alanine, β-benzisothiazoles, β-benzthiazoles, or 2-acylimino-3H-thiazoline derivatives.

The present invention further includes compositions, including pharmaceutical compositions, that include one ore more of the complexes, effector molecules, modified biological molecules and the like of the present invention together with one or more carriers, including pharmaceutically acceptable carriers. The present invention further includes methods of treating a subject including the step of administering any of these compositions such that the subject is benefited. The methods, complexes, effector molecules and other compositions of the present invention can be employed to treat any disease or disorder, including, but not limited to HIV, hepatitis, endocrine disorders, proliferative disorders, infectious disease, diabetes, emphysema, or cancer.

These and other aspects of the present invention are described in further detail hereinbelow.

BRIEF DESCRIPTION OF THE DRAWINGS

FIG. 6 is a schematic representation of the addition of PEG to a biological molecule in a site-specific manner.

DETAILED DESCRIPTION OF THE INVENTION

Figure 1A:
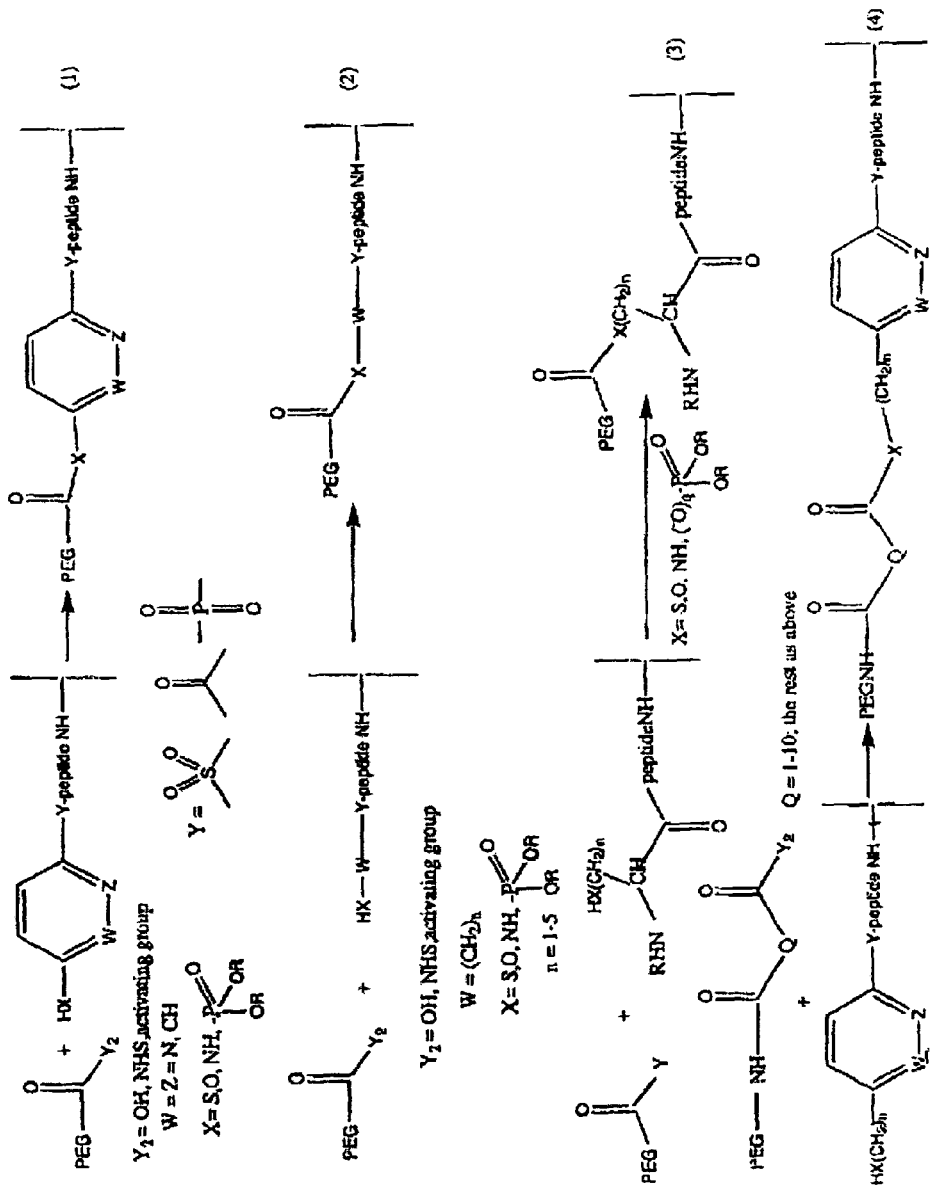
FIG. 1A-D presents specific reagents and procedures of the invention, for site-specific modification of a target reactive group in or near a target binding site on a biological molecule by covalent bonding to a functional group linked to a polyakylene oxide polymer such as polyethylene glycol (PEG). This method comprises contacting the biological molecule with a conjugate comprising the functional group linked to the polymer under conditions such that the target reactive group covalently bonds to the functional group. This conjugate of the present invention further comprises a ligand moiety that specifically binds to the target binding site on the biological molecule, thereby effecting site-specific covalent bonding of that reactive group to the functional group linked to the polymer. Panel (A) illustrates the step of attaching activated polymer (PEG) molecules to peptidyl ligand moieties ("peptide") to produce a library of conjugates comprising functional groups linked to "PEGylated" ligands. Panels (B)-(D) illustrate covalent bonding of such conjugates to a biological molecule (protein). In particular, Eqns. 5-7 and 9-11 show PEGylated proteins in which the functional group is directly linked to the PEG in such a way that the polymer becomes directly linked to the target reactive group and the ligand moiety is eliminated from the conjugate. Eqns. 8 and 12, and 13-15, present two different conjugate variations in which reaction of a target reactive group with a functional group linked to a PEGylated ligand yields a protein coupled to PEG through an intervening linker, with retention of the peptidyl ligand moiety, either as an intervening peptidyl linker (Eqns. 13-15), or as a substituent of a non-peptidyl linker (Eqns. 8 and 12). For convenient exemplification only, each peptidyl moiety in Eqns. 1-15 is shown covalently attached to a solid support (vertical bar), either directly or via PEG. Also illustrated is the fact that the protein may be conveniently biotinylated or fluorescently labeled, as shown in Eqns. 1-15 by the symbol "B". The exemplary compounds depicted in FIG. 1 are depicted on solid supports, however, these and other compounds not attached to solid supports also are within the scope of the present invention. In addition, numerous other compounds and reactions within the scope of the present invention can readily be identified based on the teaching provided in the present specification.
Figure 1B:
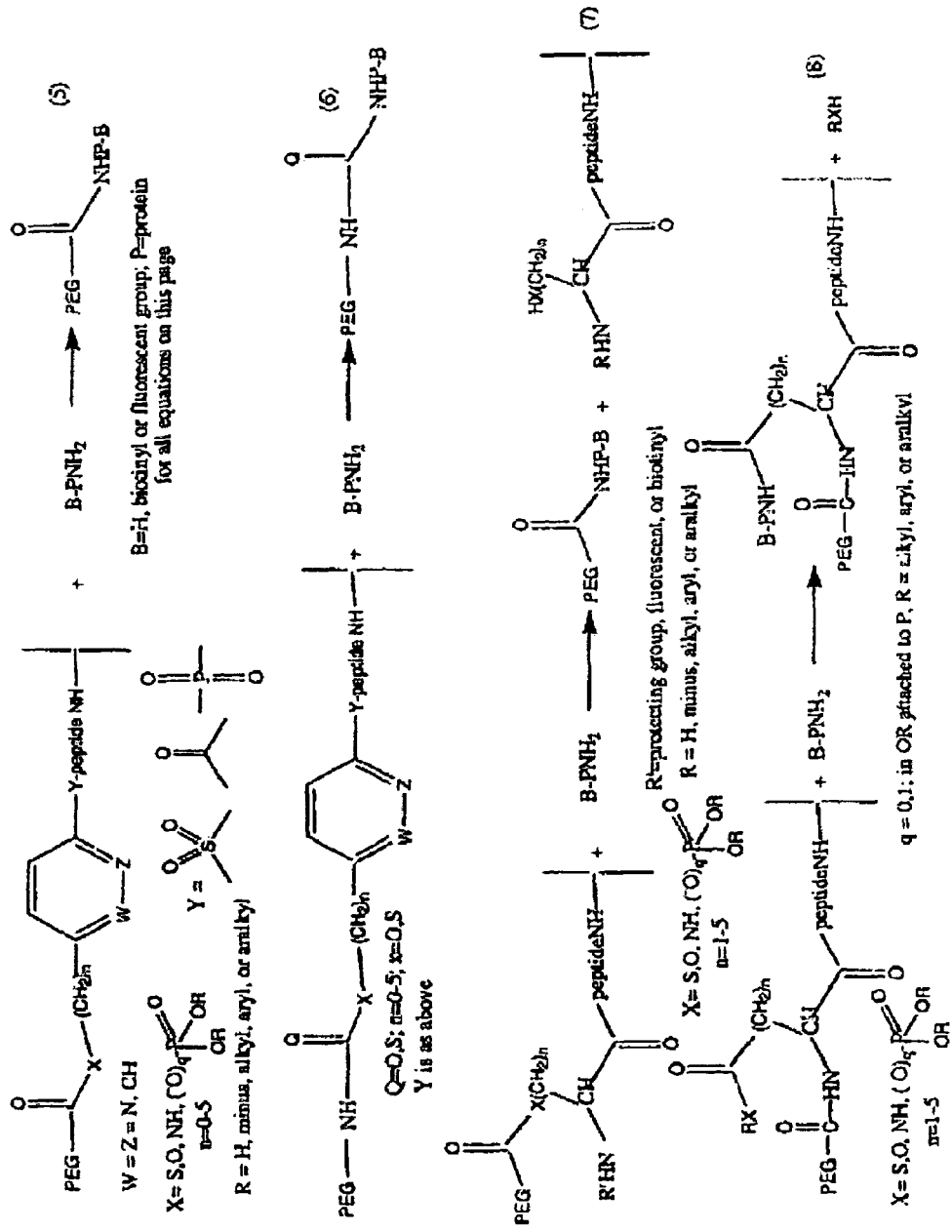
Figure 1C:
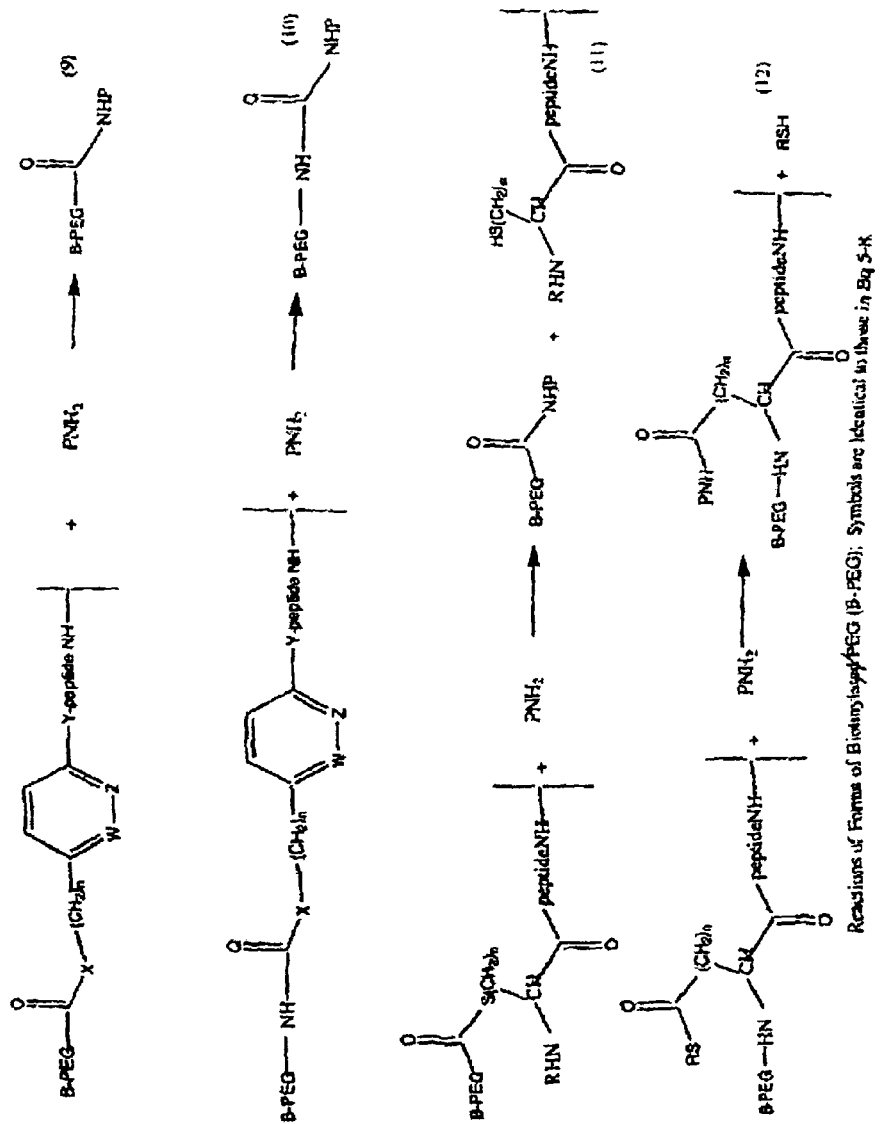
Figure 1D:
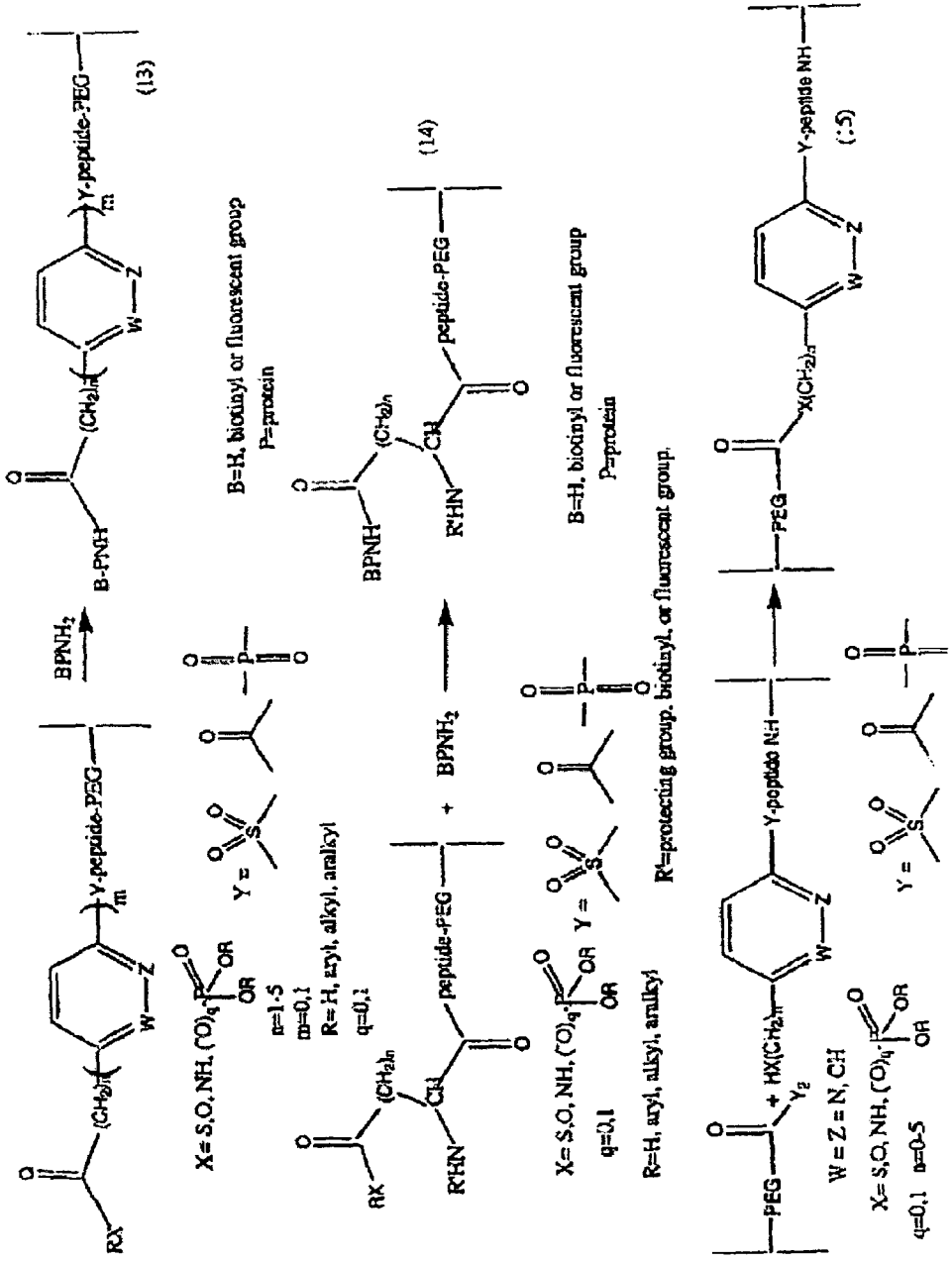

The present invention provides a way of systematically exploring the nooks and crannies of proteins and other biological molecules by revealing specific sites that can be occupied and the effects of site occupancy on protein function(s), and by screening small molecules against such specific sites, even absent any knowledge of ligand or protein structure. This technology elucidates alternate reactive "secondary ligand binding sites" that can be exploited to discover and design novel small molecule drug leads, as well as both small molecule and macromolecular-drug conjugates.

Using methods of the present invention, accessible reactive target groups, such as amine, hydroxyl or thiol groups, are identified (and mapped) anywhere on a target molecule, e.g., a protein, using probes comprising compatible reactive groups. These reactive group probes include group-specific or affinity-labeling reagents that specifically or selectively form stable covalent bonds with different target groups. Reactive group probes that are found to stably bond with target groups in a specific or selective manner can then be used to specifically or selectively modify those target groups with a functional adduct that conveys a biologically useful property (e.g., polyethylene glycol, "PEG"). The effect of contacting the protein with a potential ligand, in a combinatorial library, for instance, on the covalent bonding of a particular target group with a particular reactive group probe is also determined, to identify effector ligands that modulate this covalent bonding activity of the target group. For each effector that modulates stable covalent bonding activity of a particular target group, the extent (and, preferably, location) of noncovalent binding to the protein may be determined, to identify effectors of that target group reactivity that are noncovalently driven, as distinct from effectors that compete with the reactive group probe for covalent bonding with the target group.

An effector for a particular target group reactivity also may be tested for effects of binding on other activities of the target protein, such as an enzymatic or ligand binding activity, to identify important biological functions modulated by that effector. Such other modulated activities may directly depend upon the modulated target group reactivity, such as an enzymatic activity that depends upon a reactive group in an active site; or modulated activities may be independent of the modulated target group, such as a ligand binding activity at a site near, but not encompassing, a modulated target group. In addition, the location(s) of the binding site(s) for effectors that modulate target group reactivity and any other useful activity of the biological molecule may be determined, to define a complete structural and functional "modulatory map" of the protein or other biological target, that is, a physical map of reactive groups and ligand binding sites that are involved in various activities of the target and their modulation by noncovalently driven effectors.

The ability of the present invention to generate well-defined, more structurally diverse leads, should dramatically expedite development of novel drugs including, not only small molecule ligands, but also macromolecular conjugates, for instance, proteins specifically modified using polyethylene glycol, a drug delivery technology that can reduce immunogenic reactions to therapeutic proteins and enable them to remain in the bloodstream longer. The use of PEG as a linker moiety between proteins and small molecules, or between different proteins, is also beginning to produce exciting new products. However, numerous factors affect the bioactivity, stability and immunogenicity of PEGylated proteins and peptides: the presence or absence of linkers between the PEG and the target molecule; the nature and stability of the bond(s) between the PEG, linker and target; the impact of PEG attachment on surface charge; the coupling conditions; and the relative toxicity of the activated polymer and/or co-product(s).

Generation of regioconjugates, with PEG attached to one or more specific amino acid residue(s) would be highly advantageous in the application of PEGylation technology. Thus, each regioconjugate could be evaluated as a separate potential drug candidate, thereby permitting determination of the "best bet" for optimization of therapeutic properties of a PEGylated entity. Multiple distinct regioconjugates also would allow a choice of several isomers that appear equally viable therapeutically, or otherwise equally reasonable candidates for development. By the same token, generation of specifically coupled macromolecular conjugates comprising two or more biological molecules, for instance, a cytokine linked to a targeting antibody, with each defined species of conjugate having different combinations of distinct linkage sites on each component, would similarly expedite the application of drug targeting technology.

An ability to select different cross-linking sites on a targeting molecule, either an antibody or some other macromolecule for which no affinity labeling site comparable to that on antibodies is known, clearly would expand structural diversity of targeting conjugates, thereby broadening the range of targets and uses that could be addressed by conjugation of peptides to targeting molecules. For example, Kohler (U.S. Pat. No. 6,238,667) suggests that peptides cross-linked to an antibody may have a biological activity, such as immunostimulatory or immunoregulatory activity. In a preferred embodiment the peptide is derived from the binding site region of cytokines or complement fragments. The peptide also may comprise immunogenic epitopes for T-cells or B-cells, or be a hormone, a ligand for cytokines or a binding site derived from natural ligands for cellular receptors. The antibody may be specific for a cellular receptor on a membrane structure, such as a protein, glycoprotein, polysaccharide or carbohydrate, on normal or tumor cells.

The present invention addresses the long-felt need for a focused effort in delineating alternate binding sites on biological molecules for targeting in drug discovery and development, which need stems from the likelihood that many alternate binding sites are likely to be difficult to uncover by conventional methods. Small molecule ligands tend to concentrate at endogenous ligand binding sites, in part because such sites have evolved over hundreds of millions of years to bind physiologically relevant ligands, and often contain amino acids with altered pKa values to facilitate binding. Therefore, it is not surprising that screening for the tightest binding ligands most often results in identifying leads that are bound to endogenous ligand binding sites.

The following definitions are intended to provide guidance as to the meaning of specific terms used herein.

The term "activated polymer complex," as used herein, refers to a polymer complex that includes a functional group capable of covalent bonding to a biological molecule (e.g., a protein).

The term "primary binding site" refers to the endogenous ligand binding or active site or sites on a biological molecule. Examples of such primary binding sites include, but are not limited to, antibody binding sites, protein binding sites, and the site on an enzyme where the substrate molecule binds and where its reaction is facilitated (i.e., the catalytic domain). The term "primary binding site activity" refers to the activity of a primary binding site.

The terms "secondary binding site" and "secondary ligand binding site" are used interchangeably and refer to a site differing from the primary binding site or sites. Secondary binding sites may have no effect on the primary function of the biological molecule (a "null site"), or they may inhibit or enhance the primary function of the biological molecule.

The term "secondary site-specific," as used herein, refers to specificity to a secondary site.

"Ligand" is the general term for a molecule that noncovalently binds specifically and tightly to a complementary binding site on a target macromolecule, such as a protein, thereby forming specific macromolecule-ligand complexes. Specific interactions of proteins with ligands include receptor/ligand binding and immunoglobulin/antigen recognition. Also, interactions of enzymes with substrates, cofactors and allosteric effectors all involve specific, noncovalent binding interactions. Accordingly, many drugs are small organic molecules that noncovalently bind to a specific ligand binding site on a protein, such as a receptor or an enzyme, thereby modulating (increasing or decreasing) a biological activity of the target.

For example, screening known combinatorial libraries is not only likely to result in the highest affinity ligands binding to endogenous ligand binding sites, but it is also likely that numerous weaker binding ligands to such sites will be indistinguishable in their affinities from those ligands that bind tightest to alternate sites. Thus, many more ligands may bind modestly to endogenous ligand binding sites than ligands that bind (with similar affinities) to alternate sites. A means for determining which ligands bind to alternate sites would be very useful in many ways, especially for the development of novel therapeutics.

Even if other sites may bind ligands less tightly than endogenous ligand binding sites, they are still amenable to drug targeting once the site itself, and/or a small molecule complement to the site, is identified according to the present invention. The goal of this technology is to first, pinpoint alternate binding sites with molecular probes, and then second, discover molecules which antagonize (or agonize) these probes by competing for access to, or otherwise affecting, the same sites. Library members selected for effective antagonism against probes in the second screen are then assayed conventionally for their effects on target protein function, and for their site-specificity, for instance, using NMR spectroscopy. Once a drug-like lead emerges from the second screen, conventional and avant-garde medicinal chemical motifs may be applied to lead development and the generation of development candidates of high potency.

A powerful methodology for the development of small molecule complements that bind specifically to novel sites, therefore, emerges from such a two stage scenario. The first stage involves discovery of a specific site on a biological target molecule, the occupancy of which has functional consequences. For example a reactive entity or probe may label or tag a biological target molecule, thereby becoming irreversibly attached to a specific site. In this first stage, for a target having a known active site for enzymatic or ligand binding activity, group specific reagents that are designed to probe the entire target molecule surface for sites of attachment are used, primarily for their potential to pinpoint specific sites other than, or in addition to, known endogenous ligand binding sites. A variety of structural motifs can be employed in this first stage, in which the major goal is the potential for specifically binding and bonding to a variety of surface sites.

The objective of this first stage, therefore, is to identify molecules that attach to novel specific sites of the biological target molecule, typically using combinatorial libraries of affinity labeling molecules. For example, chemical modification reagents are particularly well suited for pinpointing specific reactive sites on surfaces. In addition, monoclonal antibodies can be used to identify reactive or nonreactive binding sites. Together, such chemical and immunological agents should provide the necessary diversity for probing target macromolecules most comprehensively.

In a second stage, combinatorial and other chemical libraries, selected for potential physiological or therapeutic properties, are used to screen against the attachment of a novel site-specific labeling agent and/or monoclonal antibody discovered in first stage screens. For example, in screening for novel small molecule therapeutics, libraries constructed around drug-like scaffolds (e.g., benzodiazepines, optimized for bioavailability in the appropriate in vivo setting), would be appropriate. The tandem screening approach of this invention is illustrated schematically in FIG. 5, using chemical modification reagents as probes in the first stage.

Figure 5:
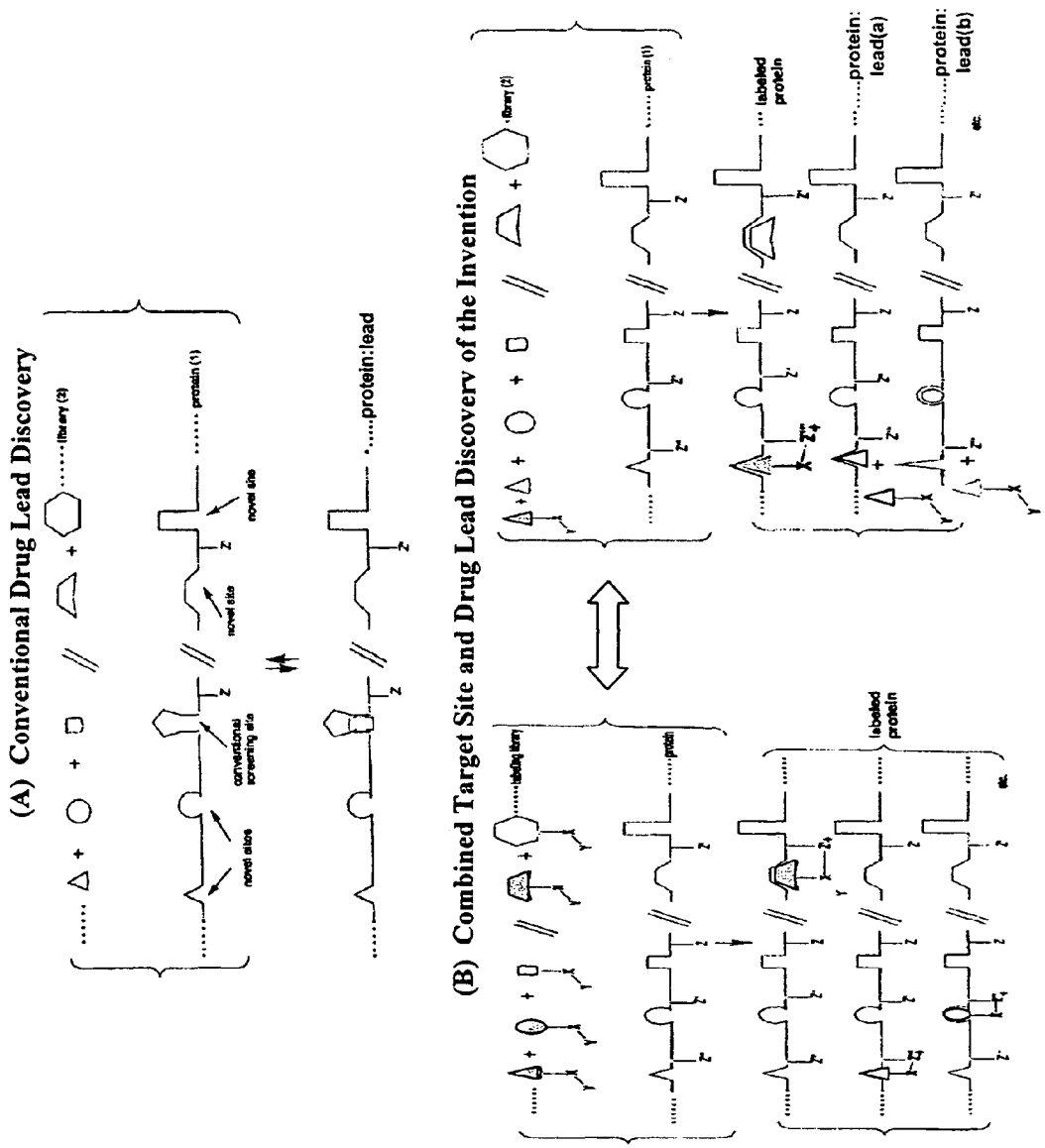
FIG. 5(A) is a schematic illustrating the general consequence of conventional lead discovery.
FIG. 5(B) is a schematic illustrating an exemplary method of novel drug lead discovery using secondary ligand binding sites.

FIG. 5 (A) depicts conventional lead drug discovery. The top row represents an idealized chemical library as a series of diverse shapes. The middle row represents the protein target as a series of potential binding sites possessing diverse shapes with one "high affinity" conventional screening (binding) site (i.e., enzyme active site). In both cases, only those shapes that are complementary to library members are shown and are meant to indicate but a subset of the protein's potential binding sites. The bottom row represents the result of contacting the protein with the full library. It is meant to indicate that with conventional screens the "high affinity" site would be the focal point of the assay, wherein binding is detected. Binding to "lower affinity" sites would generally be ignored or undetectable under such assay conditions.

FIG. 5 (B) depicts novel drug lead discovery by secondary target site discovery. The left panel describes pictorially an exemplary method for site discovery which can be accomplished with chemical libraries, or collections of group modification agents, or combinations thereof. For purposes of exposition only chemical libraries are shown. The top row represents an idealized bonding chemical library as a series of diverse shapes attached to a potentially reactive group, XY. The latter is subject to a displacement reaction by a nucleophilic amino acid side chain Z, which releases a leaving group, Y, and covalently bonds to X. (Alternatively, subject to library design, Z may covalently bond to Y.) The protein is represented as a series of potential binding sites possessing diverse shapes with proximal nucleophilic amino acid side chains, Z. (Prime superscripts are meant to indicate different environments of the same nucleophile.) In both cases, only those shapes that are complementary to library members are shown and are meant to indicate but a subset of the protein's potential binding sites.

The results of contacting the labeling library with the protein target would be to give labeled protein at rates dependent upon shape complementarity and the orientation and proximity of the Z group with respect to XY. The fastest reactions reflect specific labeling via an intermediate complex (not shown). This example is meant to show that the protein is labeled preferentially by three complementary entities at mutually distinct, novel sites. These entities and their respective labeling sites can be established by mass spectrometric and degradative techniques. (Note that this method is in contradistinction to conventional binding assays that are biased in favor of the primary binding site).

The right panel shows an exemplary method of how a specific labeling entity can be used to discover novel drug leads or inhibitors. The basis of the method is to determine the extent of bonding by the labeling entity (triangular as shown in top row) in the presence and absence of a series of shapes, embodied in a chemical library. Entities that compete for access to the triangular binding site should measurably reduce the rate of protein labeling. Entities which incorporate structural features of the labeling entity, such as the triangle, lead (a), are likely to compete for access to its binding site. Alternatively, covalent bonding could be reduced by binding of a lead (b) to an alternate site that affects the shape of the triangular site and reduces its affinity, and hence reactivity, with the labeling entity.

A preferred embodiment of the method, which employs chemical modification agents and monoclonal antibodies to identify diverse target sites, is particularly powerful in that this combined approach affords a sensitive probe of initially "low affinity sites", whether chemically reactive or not, that would generally be difficult to uncover with small molecules that merely bind, since the latter generally bind nonspecifically to multiple sites with low affinities. The structural demands of the bonding process are far more stringent than that of binding of small molecules, as the reactive group must be highly oriented for facilitated bonding, but non-reactive small molecules can bind with low affinities in multiple orientations at multiple sites.

Figure 2:
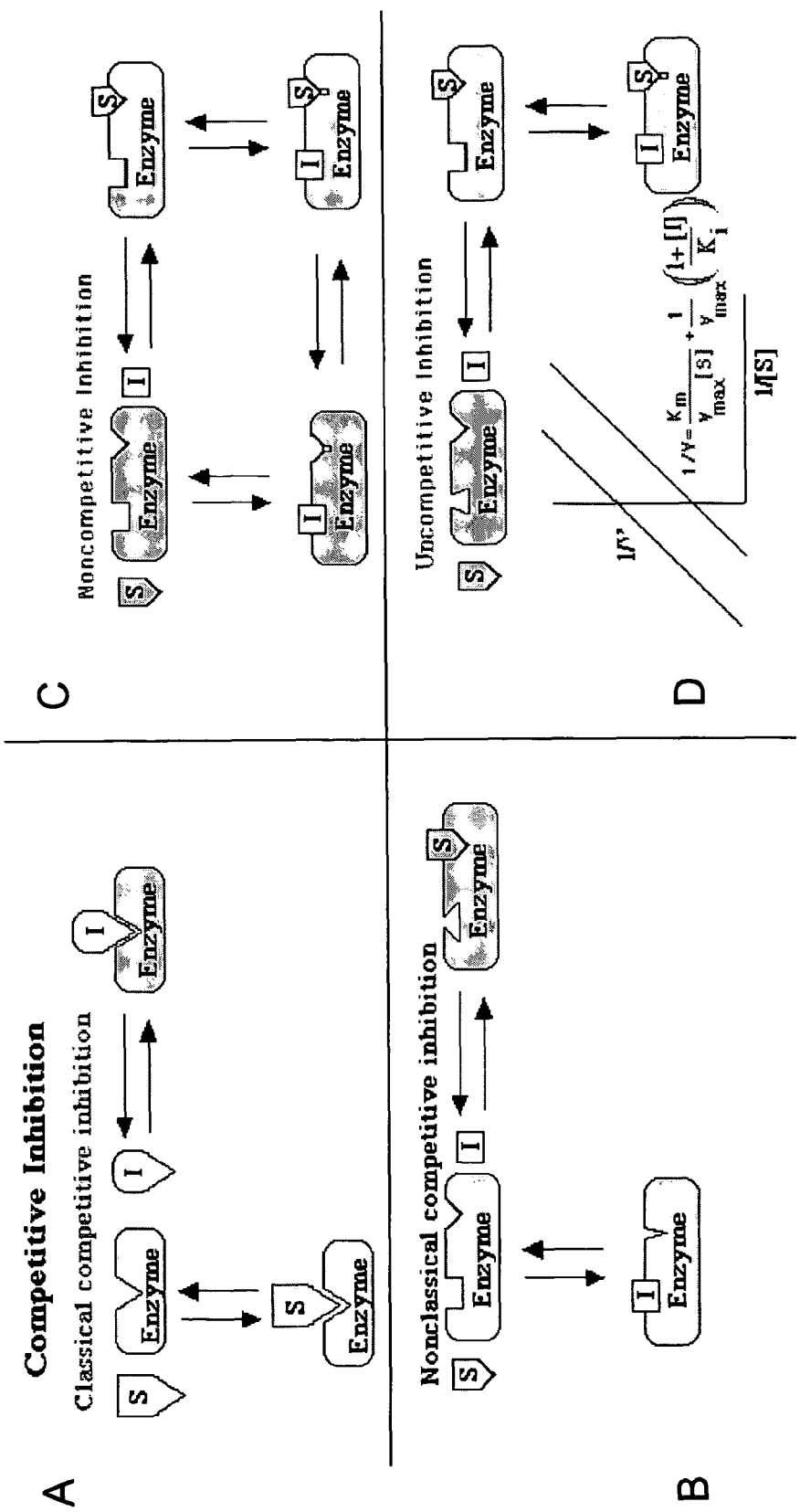
FIG. 2 presents schematic illustrations of classical competitive (A), nonclassical competitive (B), non-competitive (C), and uncompetitive (D) inhibition of substrate (S) binding to an enzyme by an inhibitor (I).
Figure 3:
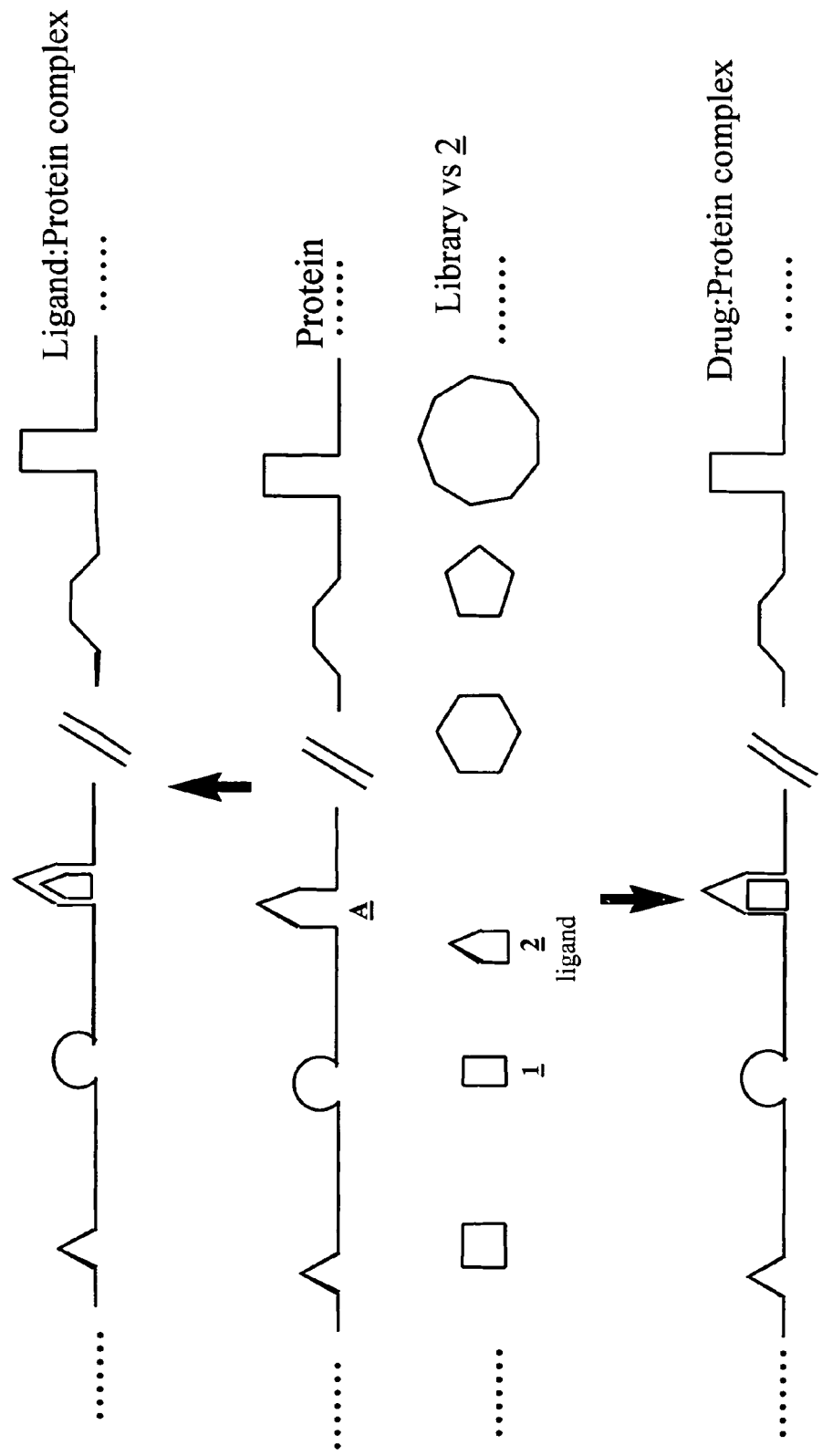
FIG. 3 schematically illustrates conventional lead drug discovery using libraries of molecules.
Figure 4:
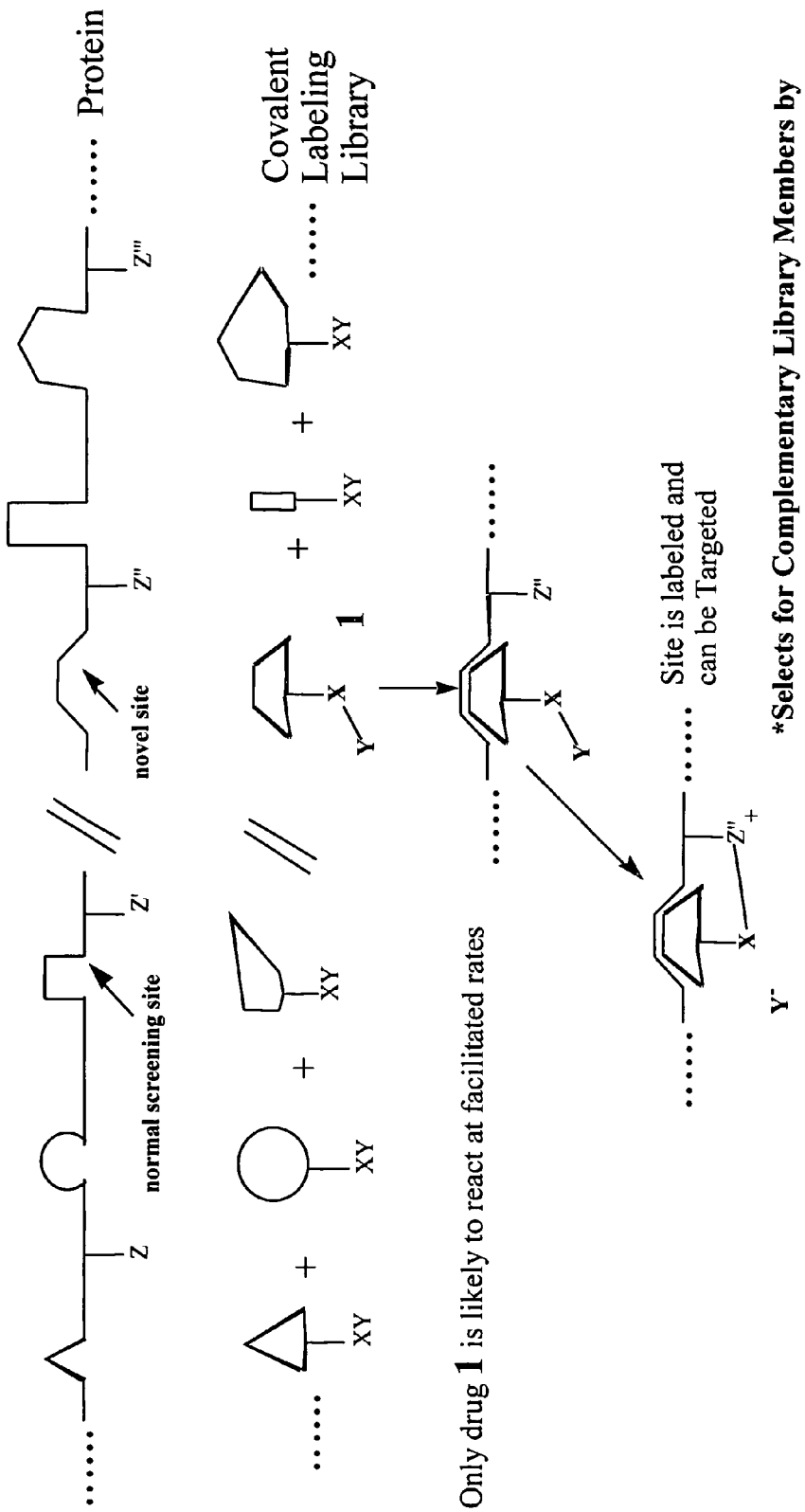
FIG. 4 schematically illustrates an exemplary method of screening a biological molecule for secondary ligand binding sites.

Enzyme inhibition generally involves the interaction of a substance with an enzyme so as to decrease the rate of the reaction catalyzed by that enzyme. Inhibitors can be classified, for example, as reversible or irreversible. Inhibitors can also be classified according to whether they are competitive, noncompetitive or uncompetitive inhibitors. FIG. 2 shows a schematic representation of classical competitive inhibition (A), non-classical competitive inhibition (B), non-competitive inhibition (C), and uncompetitive inhibition (D). In terms of kinetics, the hallmark of competitive inhibition is that excess substrate immediately, typically instantaneously, overcomes inhibition by a competitive inhibitor. A noncompetitive inhibitor allows an enzyme to bind a substrate at the same time it binds the inhibitor. A noncompetitive inhibitor acts to decrease the turnover number (i.e., the reaction rate) of an enzyme rather than to diminish the proportion of free enzyme by competing with substrate for a common binding site. Another possible category of inhibition is mixed or uncompetitive inhibition, in which the inhibitor affects the binding site and also alters the turnover number of the enzyme. Uncompetitive inhibitors bind only to the enzyme-substrate complex, not to free enzyme. In uncompetitive inhibition, the turnover number is decreased by the conversion of some molecules of enzyme to the inactive enzyme-substrate-inhibitor complex. This type of inhibition usually occurs only with multisubstrate reactions. These principles apply equally with respect to inhibition of covalent bonding on a secondary site as well as to inhibition of primary binding site activity or functional activity of a biological molecule.

The invention further contemplates using libraries to physically map potential binding sites on macromolecules. These sites can be established from determination of the locus of action of labels (discovered from first-stage screens), using standard methods of enzyme degradation/HPLC/MS of the labeled macromolecule and or NMR methods. NMR spectroscopy and X-ray crystallography are particularly valuable for determining the precise orientation of affinity groups with respect to the macromolecular site. By constructing a map of potential binding sites, one can then link entities that bind (with relatively low affinities) at proximal or contiguous sites to create molecules that bind with high affinities. See, e.g., PCT Publication WO 02/42733A2, by Erlanson et al. One aspect of the present invention therefore relates to methods of exploiting chemical modification agents so as to discover the effects of systematically labeling a specific type of amino acid (e.g., cysteine) of a biological target molecule. For instance, libraries of potential ligands are used to protect against labeling the biological target molecule, thereby revealing library molecules which specifically occupy novel binding sites that contain that type of amino acid, or that bind to a site distal to such an amino acid but nonetheless also modulate (inhibit, stimulate or activate) modification of such an amino acid.

In other words, the invention relates in part to a method for identifying a modulatable activity of a biological molecule, and an effector molecule that modulates that modulatable activity by specific binding to the biological molecule. In the first instance, the modulatable activity comprises stable covalent bonding of a target group on the biological molecule with a selected reactive group. To this end, the present invention involves tandem screening of reactive group probes against a macromolecular target, to determine the residues most vulnerable to chemical modification, followed by screening of potential ligands, to identify effector molecules that specifically modulate such chemical modifications. In this process, knowledge of the residues most vulnerable to modification can also be used to design affinity labeling libraries that incorporate the promising chemical modifiers from the first screen to site specifically label the target macromolecule.

Reactive Group Probes

The present invention therefore relates in part to a method of rationally and systematically varying the type of specific labeling entities used to identify reactive groups on a biological target molecule, such as a protein, so as to discover the effects of labeling specific amino acid types and/or occupying associated protein sites. Organic reactive groups that can serve as entities that label specific amino acid residues are well known in the art and are amply documented. See, e.g., Means. G. and Feeny. R. *Chemical Modification of Proteins*, Holden-Day, Inc.

For example, the specific reactivity of disulfides with thiol-containing amino acids can be exploited by treating a protein with a thiol-reactive molecule such as Ellman's reagent, and determining the biochemical or biological effects of such thiol-disulfide exchange. A thiol-reactive molecule that proves to be biologically active by virtue of its site-specific reactivity can then serve as a screen for chemical libraries to discover molecules that block reactivity of the disulfide at that site. In principle, this approach can be used to screen for labeling of virtually all key nucleophiles of macromolecules, including those likely to have functional consequences because of their location on the macromolecular framework. Some potentially reactive amino acid side chains (at physiological temperatures and pH) of a target protein are illustrated hereinbelow, with representative, precedented labeling entities.

To identify reactive target groups on a biological molecule such as a protein, typically the molecule is preincubated with a few equivalents of the chemical modification agent (CMA), at a concentration on the order of about one millimolar, for time $t_x$, in which either at least 50% inactivation of the protein occurs, or 50% adduct formation has occurred as judged by incorporation of CMA using mass spectroscopy (see, e.g., Krell et al., supra). Proteolytic digestion of the modified protein followed by mass analysis of the modified peptides then allows modification sites to be located. HPLC peptide mapping, with the electrospray mass spectrometer as an on-line detector, can be used to pinpoint the residues modified in covalently labeled samples. These samples are completely digested with degradative enzymes (i.e., trypsin, in the case of proteins), and the resulting peptide mixture is loaded onto a C4 reverse-phase chromatography column, which is then washed to remove denaturing agents and other very low molecular weight species. The eluent is passed through a HPLC UV/visible detector and then directly into the mass spectrometer; peptides are eluted in the usual manner with a solvent gradient following, as in Krell et al. supra, for instance. The mass spectra of the modified proteins generated from the digest of the modified protein is automatically searched for all the theoretical unmodified peptides, and this allows assignment of ions to most peaks in a map of predicted peptides in the unmodified protein. Unassigned peaks correspond to either peptides resulting from partial digestion or to modified peptides which are not cleaved at the modified residue.

Many examples are known where unadorned labeling entities are deployed as simple monomers (as group modification agents; see, e.g., Feeny and Means. supra). For instance, the reactive group of a probe for accessible target groups of the invention may be selected from any one of the following types of reactive groups: a dithioester; a thioloester; thionoester; a selenoester; a selenoloester; a selenonooester; a phosphonoester; a phosphoric ester; a phosphinic ester: a sulfonate ester; an isocyanate; a diazoester; a diazoketone; diazoamide; an acylphosphate; an imine; a thioimin; an o-salicylate; a p-salicylate; and m-salicylate; a disulfide; acetylene dicarboxylate dimethyl ester and a half ester or half amide thereof; fumaric acid or maleic acid and their esters and derivatives thereof; an a-nitroacrylic acid ester; a phenylglyoxal; a glyoxal; a 2,3-butanedione; a cyclohexanedione; an α-keto- or β-keto acid or ester; a di- or tri-fluoromethylketone; a trinitrobenzenesulfonic acid; a tetranitromethane; a diethylpyrocarbonate; an N-bromosuccinimide; a dithiothreitol; a sodium tetrathionate; a 1-ethyl-3-(3-dimethylaminopropyl) carbodiimide; an N-ethoxycarbonyl-2-ethoxy-1,2-dihydroquinoline; a fluoro-2,4-dinitrobenzene; and a (4-aminosulfonyl)-7-fluoro-2,1,3-benzoxadiazole.

Below are illustrated some specific examples of group-specific or selective reactive groups, optionally coupled to an oligomeric ligand moiety comprising a peptide or analog thereof, that are suitable for use as reactive group probes, for group- or site-specific modification of biological target molecules according to the present invention. In these examples, for convenience, the labeling entity has been appended to either a thiol, amino, hydroxyl, or carboxyl group of the peptidyl ligand moiety. For example, the amino group often forms part of an N-terminus of a peptide to which an acyl function of the labeling entity has been attached. See, e.g., formulae (5)-(9), below. Alternatively, the labeling entity can be appended directly to an amino acid side chain of the ligand that contains a thiol, hydroxyl, amino or carboxyl group, such as a cysteine, serine, lysine, or aspartate residue, respectively, rather than be separated from the peptide chain.

More in particular, to identify reactive lysine, ornithine, or histidine residues on a target molecule, compounds of formula (1), below, may be used:

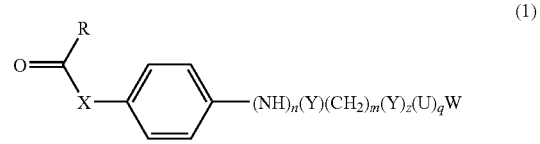

(1)

wherein: X=O, N, or S; the protons of the attached ring may be variously substituted with alkyl, aryl, or aralkyl; n=0 or 1; Y=phosphinyl, carbonyl or sulfonyl; $(U)_q$=peptidyl=(—NHCHR'CO—)$_q$, and the amino acid residues (—NHCHR'CO—), may be independently any natural or commercially available ammo acid (except lysine, ornithine, or histidine) or an enantiomer thereof, while q can vary from 2-20 (preferably 3-8); W=NR"R''' or OR", where R" and R''' can be variously H, alkyl, aryl, or aralkyl; z=0 or 1; m=0 when z=0, and m=2-6 when z is 1. R may be alkyl, aryl or aralkyl. In certain instances, e.g., for assay purposes, it is convenient to have RCO be either a fluorescent moiety or biotinylated moiety or some other readily detectable labeling moiety.

For identifying reactive lysine, ornithine, or histidine residues, compounds of the following formula (2) also may be used:

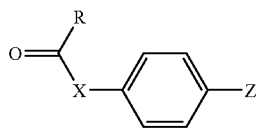
(2)

wherein: X=O, N, or S; the ring may be variously substituted para (or meta, not shown) with Z=alkyl, aryl, aralkyl, carboxyl, sulfonyl, carbamoyl, carboxamide and the like, or a fluorescent or a biotin-like moiety. R then takes the form of R"R''' N(COCHR'NH)$_n$CO(CH2)$_m$, where n=2-20, m=3-8, R" and R''' can be variously H, alkyl, aryl, or aralkyl, and the residues (COCHR'NH) may be independently any natural or commercially available amino acid or an enantiomer thereof (except lysine, ornithine, or histidine).

For identifying reactive cysteine, homocysteine and other thiol-containing residues, compounds of the following formula (3) may be used:

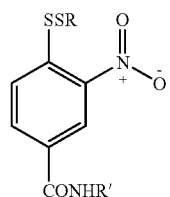
(3)

wherein: R=alkyl, aryl, and aralkyl; in certain instances, e.g., for assay purposes, R conveniently contains a fluorescent or a biotin-like or other labeling moiety; NHR'=(NHCHR"CO)$_q$W and the amino acid residues (—NHCHR"CO—) may be independently any natural or commercially available amino acid or an enantiomer thereof (except cysteine or homocysteine and other thiols), while q=2-20; W=NR'''R''', OR''', where each R''' can be variously H, alkyl, aryl, or aralkyl.

Alternatively, in formula (3), R' may be alkyl, aryl, aralkyl, or contain a fluorescent, biotinylated or other label moiety; R may be (CH2)$_n$CO(NHCHR"CO)$_q$W; the amino acid residues (—NHCHR"CO—), may be independently any natural or commercially available amino acid or an enantiomer thereof (except cysteine or homocysteine and other thiols), where W=NR'''R''' or OR'''; q=2-20 (preferably, 3-8); and n=1-8.

For identifying reactive cysteine, homocysteine and other thiol-containing residues, compounds of formulae (3A), (3B), and (3C), below, also may be used:

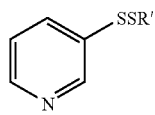
(3A)

-continued

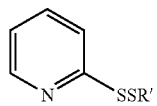
(3B)

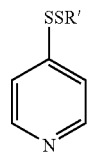
(3C)

wherein: R' may be (CH2)$_n$CONHCHR"CO)$_q$W; the amino acid residues, (—NHCHR"CO—), may be independently any natural or commercially available amino acid or an enantiomer thereof (except cysteine or homocysteine and other thiols); W=NR'''R''', OR'''; q=2-20 (preferably, 3-8); and n=1-8.

To identify reactive lysine, ornithine, cysteine, homocysteine and other primary amine or thiol-containing residues, compounds of formula (4), below, may be used:

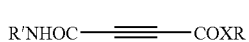
(4)

wherein: X=O or NH; R'NH=(NHCHR"CO)$_q$W; the amino acid residue (—NHCHR"CO—) may be independently any natural or commercially available amino acid or enantiomer thereof (other than lysine, ornithine, cysteine, homocysteine and other primary amines or thiols); q=2-20; W=NR'''R''' or OR''', where each R''' can be variously H, alkyl, aryl, or aralkyl. R may be alkyl, aryl, aralkyl, hydrogen, or contain a fluorescent or biotinylated or other labeling moiety.

Alternatively, in formula (4): X=NH or O; R' is alkyl, aryl, aralkyl, hydrogen, or contains a fluorescent, biotinylated or other labeling moiety; R is (CH2)$_n$CO(NHCHR"CO)$_q$W; W=NR'''R''' or OR'''; q=2-20 (preferably, 3-8); and n=1-8.

For identifying reactive lysine, ornithine, cysteine, homocysteine, histidine and tryptophan residues, compounds of the following formulae (5)-(7) may be used:

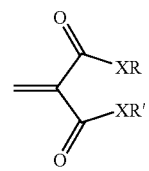
(5)

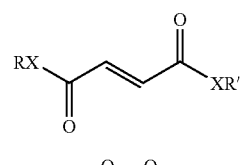
(6)

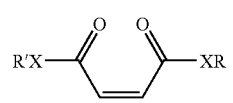
(7)

wherein: R=alkyl, aryl, hydrogen, or aralkyl, a fluorescent, biotinylated or other labeling moiety R'X=W(COCHR"NH)$_n$; n=2-20; the residues (COCHR"NH) may be independently any natural or commercially available amino acid or an enantiomer thereof (other than lysine, ornithine, cysteine, homocysteine, histidine and tryptophan), or amino acid surrogates such as 3-(2-thiazolyl)-alanine or 3-(3-benzofuranylalanine); and W=NR'''R''' or OR'''.

Alternatively, in formulae (5)-(7): R'=alkyl, aryl, aralkyl, or hydrogen, a fluorescent, biotinylated or other labeling moiety; X=O; R may be $(CH2)_nCO(NHCHR''CO)_qW$; W=NR'''R''' or OR'''; q=2-20 (preferably, 3-8); and n=1-8.

To identify reactive lysine, ornithine, trytophan, histidine, cysteine, homocysteine and other primary amine or thiol-containing residues, compounds of the following formula (8) may be used:

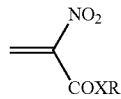

where: $RX=(NHCHR''CO)_qW$; the amino acid residues (—NHCHR''CO—) may be independently any natural or commercially available amino acid or an enantiomer thereof (other than lysine, ornithine, trytophan, histidine, cysteine, homocysteine and other primary amines or thiols), or a surrogate amino acid such as 3-(2-thiazolyl)-alanine and 3-(3-benzofuranylalanine; q=2-20; W=NR'''R''' or OR'''; each R''' can be variously H, alkyl, aryl, or aralkyl.

Alternatively, in formula (8): X=O; R=$(CH2)_nCO(NHCHR''CO)_qW$; W=NR'''R''' or OR'''; q=2-20 (preferably, 3-8); and n=1-8.

To identify reactive lysine, ornithine, cysteine, homocysteine, histidine and tryptophan residues, compounds of the formulae (9) and (10), below, may be used:

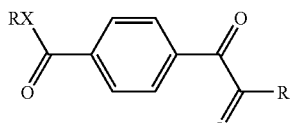

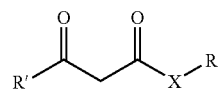

where, in formula (9): R=hydrogen, W, alkyl, aryl, or aralkyl, or contains a fluorescent, biotinylated or other labeling moiety; $R'X=R''NH=(NHCHR''CO)_qW$; the residues (COCHR''NH) may be independently any natural or commercially available amino acid or an enantiomer thereof (other than lysine, ornithine, cysteine, homocysteine, histidine and tryptophan), or an amino acid surrogate such as 3-(2-thiazolyl)-alanine or 3-(3-benzofuranylalanine); q=2-20; W=NR'''R''' or OR'''; where each R''' is variously H, alkyl, aryl, or alkyl.

Alternatively, in formula (9): R=$(NHCHR''CO)_qW$; q=2-20; R'X=alkyl, aryl, aralkyl, W or contains a biotinylated or other labeling moiety; W=NR'''R''' or OR'''; where each R''' is variously H, alkyl, aryl, or aralkyl.

In another alternative for formula (9): $R'X=R'O=O(CH2)_m(CO)(NHCHR''CO)_nW$; m=3-6; n=2-20; W=NR'''R''' or OR''', where each R''' can be variously H, alkyl, aryl, or aralkyl or contain a fluorescent, biotinylated or other labeling moiety; R=H, alkyl, aryl, aralkyl, W, or contains a fluorescent, biotinylated or other labeling moiety.

In formula (10): RX=hydrogen, W, alkyl, aryl, or aralkyl, or contains a fluorescent, biotinylated or other labeling moiety; R1=$(NHCHR''CO)_qW$; q=2-20; W=NR'''R''' or OR''', where each R''' is variously H, alkyl, aryl, or aralkyl.

Alternatively, in formula (10): RX=$(NHCHR''CO)_qW$; q=2-20; R'-hydrogen, alkyl, aryl, or aralkyl, W or contains a fluorescent, biotinylated or other labeling moiety; W=NR'''R''' or OR''', where each R''' is variously H, alkyl, aryl, or aralkyl.

In another alternative for formula (10), $RX=O(CH2)_m(CO)(NHCHR''CO)_nW$; m=3-6; n=2-20; W=NR'''R''', OR''', where each R''' is variously H, alkyl, aryl, or aralkyl or fluorescent, biotinylated or other labeling moiety; R=H, alkyl, aryl, aralkyl, W, or contains a fluorescent, biotinylated or other labeling moiety.

For identifying reactive lysine, ornithine, cysteine, homocysteine, histidine and tryptophan residues, compounds of the following formulae (11A), (11B) or (12) may be used:

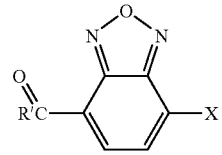

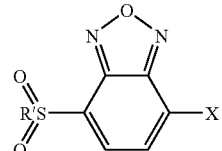

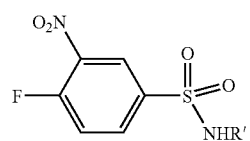

where, in formulae (11A) and (11B): X=halo; R'=$(NHCHR''CO)_qW$; q=2-20; W=NR'''R''', OR''', where each R''' can be variously H, alkyl, aryl, or aralkyl.

Alternatively, for formulae (11A) and (11B): R'=$O(CH2)_m(CO)(NHCHR''CO)_nW$; m=3-6; n=2-20; W=NR'''R''' or OR''', where each R''' is variously H, alkyl, aryl, aralkyl or contains a fluorescent, biotinylated or other labeling moiety.

In formula (12): R'NH=$(NHCHR''CO)_qW$; q=2-20; W=NR'''R''' or OR''', where each R''' is variously H, alkyl, aryl, or aralkyl.

Potential Ligand Libraries

Typically, for screening potential ligands for binding and effects of target group reactivity or other activity of a biological target molecule, such as a protein, chemical libraries containing sufficient excess of each library member to bind to 50% of a target molecule at 80 µM are pre-incubated with the latter and then, at time t, the reaction chemical modification agent is added to the mixture. At time t (sufficient to cause 50-80% labeling of the unprotected protein), the activity of the protein is determined by separating the small molecule fraction from the protein, or adding substrate in vast excess and measuring residual activity. The extent of protection of the protein by library members is determined by residual activity.

Many libraries of potential ligands that may be screened in the present invention are known in the art. For instance, U.S. Pat. No. 6,277,583B1 to Krantz et al. discloses affinity labeling libraries, including oligomeric molecules, suitable as potential ligands for screening to find effector molecules according to the present invention. Similarly, PCT Publication Number WO 00/00823 by Wells et al. and corresponding U.S. Pat. No. 6,335,155B1 to Wells et al. both disclose methods for small organic molecule ligands suitable for screening with this invention. Further, U.S. Pat. Nos. 5,582,981 to Toole et al. and 6,180,348 to Li, disclose oligonucleotide aptamers suitable for screening as potential ligands of this invention. Furthermore, Blum, J. H. et al., "Isolation of peptide aptamers that inhibit intracellular processes", Proc. Natl. Acad. Sci. U.S.A. 97:2241-2246 (2000), discloses random peptide sequences suitable for potential ligands of the present invention.

Inactivation Studies of HIV Protease I

One exemplary application of the invention methods is development of new classes of inhibitors for HIV. The following analyses of previous inactivation studies on HIV protease I provide support for applying the present approach to the problem of finding additional inhibitors of this target, as well as novel drug leads for other biological target molecules.

Targeting Cys95. Both glutathione (I) and 5,5'-dithiobis(2-nitrobenzoic acid) (II) are known to inactivate HIV protease I by covalent attachment to Cys95 at the dimer interfaces. Davis et al. *Biochemistry* 20:2482-2488 (1996). For quantification of the irreversible inactivation of HIV proteases by these disulfides, HIV-1 PR (15 µg/ml final concentration) was preincubated at 25 C in 50 mM HEPES (pH 8.0), 1M NaCl, 1 mM EDTA, 5% $Me_2SO$ in the presence of a 10 µM to 1 mM concentration of each inhibitor. At various times, aliquots were removed and assayed for activity. The rates of inactivation were calculated after Salto et al. *J. Biol. Chem.* 269: 10691-10698 (1994).

Combinatorial libraries containing tetrapeptides were synthesized with free C and N termini using T, L, N, F, R, S, V, G, F Q, and H as amino acid residues randomly located at the four positions of $P_4P_3P_2P_1$ according to procedures well known in the art (Houghten, R. A. *Annu. Rev. Pharmacol. Toxicol.* 2000, 40:273-282 and references therein). The amino acids were either spatially separated or synthesized in 100 pools of 100 tetrapeptides. Libraries were screened against glutathione or II by preincubating the tetrapeptide(s) with HIV PR then adding the disulfide and waiting until time $t^\wedge$ has elapsed (the time required to inhibit 50-75% of the biological target molecule's activity) in the absence of the library. The most active compounds using the assay in Salto et al. proved to be S-F-N-L (Seq. ID 1) and TLNL (Seq. ID 2) (100 µM) which bind at the dimer interface (Schramm et al. *Biochem. Biophys. Res. Commun.* 194:593-600 (1993)).

Targeting Cys67 and His69. Cupric ions are known to specifically inactivate HIV I protease by binding to Cys67 and His69 (Danielson et al. *Adv. Exp. Med. Biol.* 463:99-103 (1998)). Inhibition of HIV PR was measured according to Danielson et al.: copper was added as $CuCl_2$.

Combinatorial libraries of octapeptides were synthesized using T, L, N, F, S, G, F Q, V and I at positions 3-6 to generate 10,000 octapeptides. E and I occupied positions 1 and 2, respectively, and G, L occupied positions 9 and 10, respectively. The C-terminus was in amide form, and the N terminus was in amino form. The peptide libraries were synthesized by standard procedures known in the art, Houghten, supra. The libraries were screened against HIV PR with and without $CuCl_2$. $CuCl_2$ was added to block 50-75% activity. Libraries were screened against $CuCl_2$ by preincubating the tetrapeptide(s) with HIV PR, then adding $CuCl_2$ at $t_0$ and waiting until time $t_x$ has elapsed, the time required to inhibit 50-75% of enzyme activity in the absence of the library. At $t_x$ residual HIV PR activity was measured according to Danielson et al, supra, after adding cupric ion scavenger, namely, iminodiacetic. An example of an inhibiting peptide of HIV PR which is non-substrate based, that exhibited inhibitory activity in the vicinity of about 5 µM, is $LGQGVSIE-NH_2$ (Seq. ID 3).

Chemospecificity of Modification of a Protein. For conjugation of a selected biological target molecule (e.g., a protein as described infra) to another molecule, such as polyethylene glycol ("PEG") or a targeting entity, chemical modifiers that do not significantly alter biological activity of the biological target molecule are preferred. A library of minimally sized probes for chemically reactive groups is screened for reactivity with the target molecule. Reactive groups that covalently bond to the target but do not undesirably alter biological activity are then incorporated into a series of libraries, each of which is screened against the macromolecular target to discover affinity labels specific for individual residues that also do not alter biological activity. The affinity labels are then employed in conjunction with the conjugating (e.g., targeting) entity to selectively label the protein, as illustrated, for instance, in FIG. 1.

As shown in Equations (1)-(15) in FIG. 1, one method of site-specific modification according to the invention involves attaching a form of PEG to a framework consisting of a variable group (which can be oligomeric, such as peptidyl, peptoidyl, oligonucleotidyl, or carbohydrate, or a small non-oligomeric organic molecule) and a bridging moiety. The variable group may have affinity to a site on the protein by virtue of complementarity to such a site. For purposes of exposition herein, the variable group will be assumed to be peptidyl. PEG may either be attached directly to the variable group or to a bridge. The PEG group may form part of a potentially reactive entity with or be in stable linkage with the variable group and/or the bridge. The potentially reactive labeling entity to be generated may be an active ester or thioester or various Michael acceptors known in the art. The peptidyl group, which can have from 2-20 amino acids (of D or L configuration), can be varied as the variable group. The variable group forms a segment of composite PEG-linked reagents to be reacted with target protein. Some of these ensembles of PEGylated molecules (e.g., PEG-linked reagents as described supra) are then tantamount to ensembles of activated PEGs, which are differentiated by the structure of the peptidyl group. In several iterations, PEG may form part of a potentially reactive linkage (e.g., the potentially reactive entity described supra) with the peptidyl group or the bridge (Eqns. 5-7 and 9-11). Transfer of PEG to the target protein results in a PEGylated protein devoid of the bridge and variable moiety, in which the PEG is attached directly to protein. Alternatively, PEG may be attached in stable linkage to the variable group, and may not be a part of the potentially reactive entity (Eqn. 8). The protein is then condensed onto a framework bearing PEG.

The synthetic plan involves the attachment of PEG close to the variable component, which serves as a template, or chiral auxiliary, to induce specific reactions. The synthetic plan can be accomplished in a variety of ways, with PEG either attached to a center undergoing reaction, or in stable linkage to a component (Eqns. 8, 12), which ultimately serves as a bridge or linker between PEG and the biological entity introduced onto the reacting framework.

Synthesis of PEG substrates can be accomplished in a number of cases by linking PEG in its commercially available amino or Carboxyl forms in the final step of the synthesis.

(Only the para forms are shown for coupling to aromatics, but meta forms are also the basis of this disclosure). For example, PEG carboxyl ($Y_2$=OH) in Equation 1 can be coupled to either phenolic, thiophenolic, anilino, or, in Equation 2, to thioalkyl or alcoholic atoms, by standard coupling reactions involving carbodiimide chemistry or PEG active ester condensations. As well, acyl phosphates or phosphonates (Eqns. 1-4, R=H, aryl, alkyl, and aralkyl) as active esters can be prepared by standard methods known in the art and used as substrates for specific reactions with target proteins. Alternatively, PEG-$NH_2$, may either (1) be linked in amide form to a carboxyl moiety by pretreating it with a cyclic anhydride or the like, and then coupling the resulting carboxylic acid to the variable component (Eqn. 4), or (2) by condensing it with isocyanates or thioisocyanates (not shown). In an entirely analogous sequence (not shown), PEG-SH can be condensed by reaction with cysteine thiols or coupled in other ways to a partner to give disulfides or thioethers, which, in turn may be used to link the biologically active moiety (e.g., the biological target molecule as described supra) to PEG or the PEG carrier.

The ultimate objective of regiospecific attachment of protein to PEG directly, or through a bridge, may be conveniently achieved using solid phase or solution synthesis as shown in Equations 5-14. In some instances it may be advantageous to execute a strategy in which both PEG and protein are anchored to independent supports, undergo reaction, and, for ease of assay, product can be freed from the supports sequentially (Eqn. 15).

Equations 5-8 show PEG substrates in various modes of reactivity that either result in transfer of PEG to the protein (Eqns. 5-7) or lead to condensation of protein on the linker framework (Eqn. 8). Equations 9-12 relate to analogous reactions of biotinylated or otherwise labeled PEG (shown for B=H, biotinyl, absorptive or fluorescent group).

In yet another approach, PEG can be anchored to a solid support at one end (Eqns. 13-14), and the variable moiety can then serve as a bridge to the protein, the latter being introduced by reaction with ester, or condensed onto the Michael acceptor (not shown). As shown in Equations 13 and 14, respectively, the protein can be separated by a bridging group or linked directly to the variable moiety. Achieving specific points of attachment on the variable group involves differentially freeing protecting groups to enable activation of specific positions on the variable group.

The PEG molecule can be attached to the target molecule either in solution or when anchored to a solid phase. In the latter case, PEG is attached at one end to a solid phase or support such as a bead; the other end is linked, by standard chemistries known in the art, to a variable moiety which serves as a potential affinity group to a site on the target protein.

The activated PEG molecule is treated with the target protein for a fixed time frame and the mixture is then washed to remove unreacted protein and any free reaction products. If the protein is specifically biotinylated, the extent of reaction can be monitored with biotin-avidin technology, e.g., avidin-horse radish peroxidase conjugates. Alternatively, if antibodies to the protein are available, they can be used to assay for bound protein.

In another variant, the target protein is specifically anchored to a solid support and treated with biotinylated forms of activated PEG peptide libraries. The extent of reaction can then be read out using avidin-biotin technology as above.

In solution, activated PEG molecules can be incubated with biotinylated protein (or biotinylated PEG molecules can be incubated with protein), and then transferred to wells containing antibodies that allow capture of the protein, which can be read out with biotin-avidin technology. Since protein-PEG conjugation involves a substantial increase in mass, the reaction could also be monitored by mass spectrometry and/or BPLC.

The conjugation of PEG to target protein can be carried out in pools or with spatially separated PEG molecules. If the reaction is carried out in pools, standard deconvolution methodology, known in the art, is used to establish the structures of rapidly reacting PEG-linked moieties. Those wells that exhibit the greatest percentage PEGylation are assumed to be prime candidates for specific reactions, based on the notion that specific affinity moieties are accelerating the rapid reactions relative to a standard lacking an affinity group.

A number of techniques can be used to establish that PEG is linked to a specific residue of the protein target. The most direct is by NMR spectroscopy and can be easily employed if the resonances of the protein have been assigned. In several instances above the reactive carbonyl can be specifically labeled with C-13 or C-14, and either NMR or radioactive techniques can be used to follow the label.

Alternatively, standard trypsin or other enzymatic digests (in conjunction with peptide characterization conveniently performed with mass spectrometry), can be used to determine the precise point of attack on the parent protein.

The above technology is relevant to any molecule in which it is necessary to differentiate among functional groups of the same type which are located in different environments. In addition to proteins, these may be peptides, such as chemokines or cytokines, carbohydrates, oligonucleotides, antisense molecules, or organic molecules. Specific examples of PEGylated molecules of clinical interest include interferons, interleukins, various decoy receptors such TNF-ct receptor, various monoclonal antibodies, and various small molecules that possess short duration of action whose lifetimes or immunogenicity can be altered favorably by attachment to PEG.

The entirety of each patent or other publication cited herein is hereby incorporated herein by reference for the purpose of disclosing known materials and methods that are suitable for the practice of the present invention.

The present invention having now been fully described with reference to representative embodiments and details, it will be apparent to one of ordinary skill in the art that changes and modifications can be made thereto without departing from the spirit or scope of the invention as set forth herein.

What is claimed is:

1. A method for modification of a target group in or near a secondary ligand binding site of a protein comprising:

contacting the protein with at least one site-specific activated polymer complex comprising:

a functional group reactive with the target group; a polymer linked to the functional group; and a ligand moiety that specifically binds to the secondary ligand binding site, thereby effecting site-specific covalent bonding of the target group on the protein via the functional group, and eliminating the ligand moiety from the protein-polymer conjugate after the specific covalent bonding of the target group on the protein, wherein the functional group is selected from the group consisting of: a dithioester; a thioloester; thionoester; a selenoester; a selenoloester; a selenonooester; a phosphonoester; a phosphoric ester; a phosphinic ester; a sulfonate ester; a diazoester; an acylphosphate; an o-salicylate; a p-salicylate; a m-salicylate; a disulfide; and an $\alpha$-keto- or $\beta$-keto acid or ester;

wherein the polymer is a polyethylene glycol polymer;

wherein the secondary site-specific ligand moiety is a peptidyl ligand moiety or carbohydrate ligand moiety; and wherein the secondary ligand binding site is a site differing from a primary binding site; and wherein the secondary ligand binding site has no effect on the primary function of the protein.

2. The method of claim 1, wherein the protein comprises a plurality of secondary ligand binding sites, and the ligand moiety binds to only one of the plurality of secondary ligand binding target sites.

3. The method of claim 1, wherein the protein is contacted with the activated polymer complex in the presence of at least one other molecule comprising at least one other reactive group that covalently bonds to the functional group, and the ligand moiety is selected to avoid binding that would effect covalent bonding of the other reactive group to the functional group linked to said polymer.

4. The method of claim 1, wherein the ligand moiety of the activated polymer complex is a peptidyl ligand moiety.

5. The method of claim 4, wherein the functional group of the activated polymer complex is directly linked to the polymer so that the polymer becomes linked via the functional group directly to the target group and the peptidyl ligand moiety does not become linked to the protein.

6. The method of claim 5, wherein said activated polymer complex is selected from the group consisting of

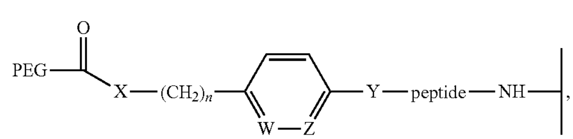

,

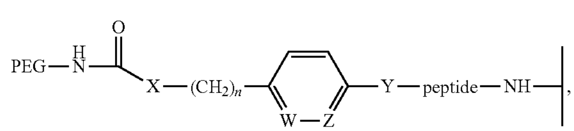

,

-continued

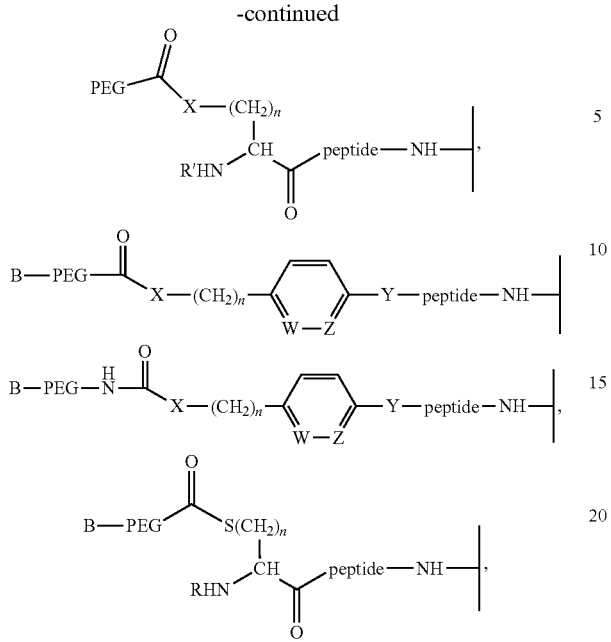

wherein B is selected from the group consisting of hydrogen, biotinyl and a fluorescent group, and
Q is O or S;
W and Z are each independently N or CH;
X is selected from the group consisting of S, O, NH and

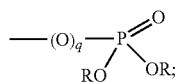

q is 0 or 1;
R is selected from the group consisting of hydrogen, aryl, alkyl and aralkyl;
Y is selected from the group consisting of

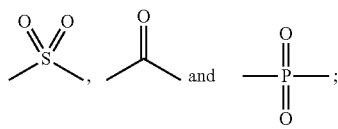

R' is selected from the group consisting of a protecting group, a biotinyl and a fluorescent group; and n is an integer from 0 to 5.

7. The method of claim 1, wherein a intervening linker is linked to the peptidyl ligand moiety that becomes linked to the protein such that the intervening linker comprises no peptidyl bond of the peptidyl ligand moiety.

8. The method of claim 7, wherein the activated polymer complex is selected from the group consisting of

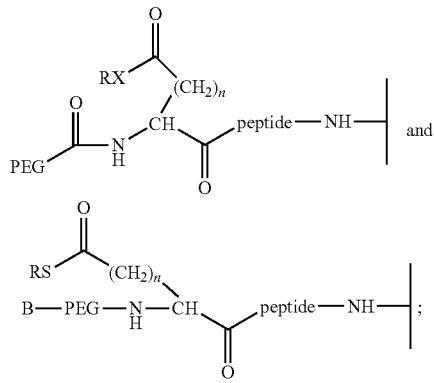

wherein
B is selected from the group consisting of hydrogen, biotinyl and a fluorescent group;
X is selected from the group consisting of S, O, NH and

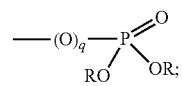

q is 0 or 1;
R is selected from the group consisting of hydrogen, aryl, alkyl and aralkyl;
n is an integer from 1 to 5.

9. The method of claim 4, wherein the peptidyl ligand moiety is further linked reversibly to a solid support, either directly or via the polymer.

10. The method of claim 1, wherein reactivity of the functional group is photochemically induced.

11. The method of claim 4, wherein the peptidyl ligand moiety comprises at least one synthetic amino acid or one surrogate amino acid.

12. The method of claim 11, wherein the synthetic amino acid is selected from the group consisting of: β-alanine, γ-aminobutyrate, O-methyl-substituted threonine, O-methyl-substituted serine, and O-methyl-substituted tyrosine.

13. The method of claim 11, wherein the surrogate amino acid is selected from the group consisting of β-thiazolealanine, β-thiadiazole-alanine, β-isothiazole-alanine, β-isoxazole-alanine, oxazole-alanine, β-benzoxazole-alanine, β-benzisoxazole-alanine, β-benzisothiazoles, β-benzthiazoles, and 2-acylimino-3H-thiazoline derivatives.

* * * * *